US009000420B2

(12) United States Patent
Kim et al.

(10) Patent No.: US 9,000,420 B2
(45) Date of Patent: Apr. 7, 2015

(54) CONDENSED-CYCLIC COMPOUND AND ORGANIC LIGHT EMITTING DIODE INCLUDING ORGANIC LAYER CONTAINING THE CONDENSED-CYCLIC COMPOUND

(75) Inventors: Hee-Yeon Kim, Yongin (KR); Seung-Gak Yang, Yongin (KR); Kwan-Hee Lee, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 426 days.

(21) Appl. No.: 12/895,732

(22) Filed: Sep. 30, 2010

(65) Prior Publication Data
US 2011/0084256 A1    Apr. 14, 2011

(30) Foreign Application Priority Data
Oct. 9, 2009 (KR) .................. 10-2009-0096393

(51) Int. Cl.
*H01L 29/08* (2006.01)
*C07D 213/06* (2006.01)
(Continued)

(52) U.S. Cl.
CPC .............. *C07D 213/06* (2013.01); *C07C 13/62* (2013.01); *C07C 211/61* (2013.01);
(Continued)

(58) Field of Classification Search
USPC .......................................... 257/40
See application file for complete search history.

(56) References Cited

U.S. PATENT DOCUMENTS

2004/0241496 A1* 12/2004 Zheng et al. ............. 428/690
2008/0124455 A1*  5/2008 Shin et al. ................. 427/66

(Continued)

FOREIGN PATENT DOCUMENTS

JP    2010-073987 A    4/2010
JP    2010-111620 A    5/2010

(Continued)

OTHER PUBLICATIONS

C. A. Henriques, "Characterization of the Coke Formed During o—Xylene Isomerization over Mordenites at Various Temperatures" Jul. 31, 1997, Journal of Catalysis, 172, p. 436 and 437.*

(Continued)

*Primary Examiner* — Caleb Henry
(74) *Attorney, Agent, or Firm* — Knobbe Martens Olson & Bear LLP

(57) ABSTRACT

A condensed-cyclic compound represented by Formula 1 below and an organic light emitting diode including the condensed-cyclic compound:

21 Claims, 1 Drawing Sheet
Formula 1
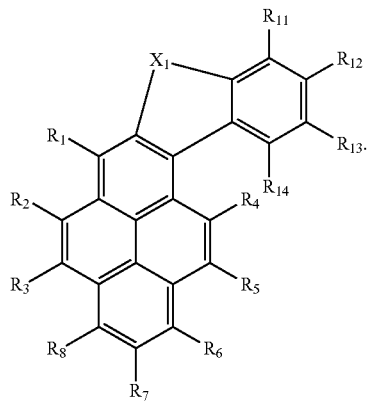

(51) Int. Cl.

| | |
|---|---|
| *C07C 13/62* | (2006.01) |
| *C07C 211/61* | (2006.01) |
| *C07D 213/22* | (2006.01) |
| *C07D 235/08* | (2006.01) |
| *C07D 401/04* | (2006.01) |
| *C07D 487/04* | (2006.01) |
| *H01L 51/00* | (2006.01) |
| *H01L 51/50* | (2006.01) |

(52) U.S. Cl.
CPC ........... *C07D 213/22* (2013.01); *C07D 235/08* (2013.01); *C07D 401/04* (2013.01); *C07D 487/04* (2013.01); *H01L 51/0056* (2013.01); *H01L 51/5048* (2013.01); *H01L 51/5052* (2013.01); *C07C 2103/18* (2013.01); *C07C 2103/54* (2013.01)

(56) References Cited

U.S. PATENT DOCUMENTS

| | | | |
|---|---|---|---|
| 2008/0274303 A1* | 11/2008 | Agata et al. | 428/1.1 |
| 2008/0299294 A1* | 12/2008 | Yen | 427/66 |
| 2009/0096356 A1 | 4/2009 | Murase | |
| 2011/0204354 A1 | 8/2011 | Sekiguchi et al. | |

FOREIGN PATENT DOCUMENTS

| | | |
|---|---|---|
| JP | 2010-205986 | 9/2010 |
| KR | 10-2006-0117038 A | 11/2006 |
| KR | 10-2006-0118913 A | 11/2006 |
| KR | 10-2007-0003586 A | 1/2007 |
| KR | 10-2007-0093401 A | 9/2007 |
| KR | 10-2008-0047209 | 5/2008 |
| KR | 10-2009-0042272 A | 4/2009 |
| WO | WO 2010/053210 A1 | 5/2010 |

OTHER PUBLICATIONS

Seung Jun Hwang, "Highly Efficient and Versatile Synthesis of Polyarylfluorenes via Pd-Catalyzed C—H Bond Activation", Aug. 10, 2009, KAIST, vol. 11, pp. 4588-4591.*

European Patent Office, Extended European Search Report corresponding to U.S. Appl. No. 12/895,732 dated Dec. 13, 2010, 9 pages.

C.A. Henriques, J.L.F. Monteiro, P. Magnoux and M. Guisnet, Characterization of the Coke Formed During o-Xylene Isomerization over Mordenites at Various Temperatures, Journal of Catalysis, 1997, pp. 436-445, Academic Press.

Seung Jun Hwang, Hyun Jin Kim and Sukbok Chang, Highly Efficient and Versatile Synthesis of Polyarylfluorenes via Pd-Catalyzed C—H Bond Activation, Organic Letters, 2009, pp. 4588-4591, vol. 11, No. 20, Department of Chemistry, Korea Advanced, Institute of Science and Technology (KAIST, Daejeon, Korea.

Official Action issued by the Korean Industrial Property Office dated Jul. 29, 2011 in Korean Patent Application No. 10-2009-0096393, 5 pages.

Seung Jun Hwang, Hyun Jin Kim and Sukbok Chang, Highly Efficient and Versatile Synthesis of Polyarylfluorenes via Pd-Catalyzed C—H Bond Activation, Organic Letters, Aug. 10, 2009, 4588-4591, vol. 11, No. 20, American Chemical Society.

Official Action from the Japanese Patent Office dated Dec. 18, 2012 in the examination of Japanese Patent Application No. 2010-225742, 3 pages.

* cited by examiner

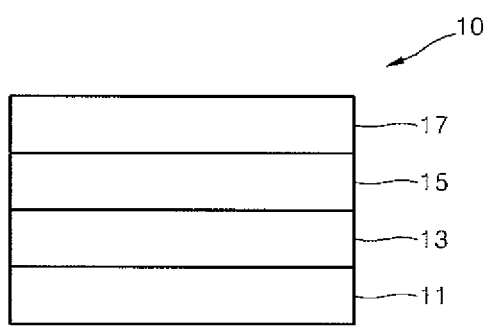

CONDENSED-CYCLIC COMPOUND AND ORGANIC LIGHT EMITTING DIODE INCLUDING ORGANIC LAYER CONTAINING THE CONDENSED-CYCLIC COMPOUND

CROSS-REFERENCE TO RELATED APPLICATIONS

This application claims the benefit of Korean Patent Application No. 10-2009-0096393, filed on Oct. 9, 2009, in the Korean Intellectual Property Office, the disclosure of which is incorporated herein in its entirety by reference.

BACKGROUND

1. Field

A condensed-cyclic compound, and an organic light emitting diode including an organic layer containing the condensed-cyclic compound are provided.

2. Description of the Related Technology

Organic light-emitting diodes (OLEDs), which are self-emitting devices, have advantages such as a wide viewing angle, excellent contrast, quick response, high brightness, excellent driving voltage characteristics, and can provide multicolored images.

A typical OLED has a structure including a substrate, and an anode, a hole transport layer (HTL), an emissive layer (EML), an electron transport layer (ETL), and a cathode which are sequentially stacked on the substrate in the order stated. In this regard, the HTL, the EML, and the ETL are organic thin films formed of organic compounds.

An operating principle of an OLED having the above-described structure is as follows.

When a voltage is applied to the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF CERTAIN INVENTIVE ASPECTS

A compound for providing an organic light emitting diode having high efficiency and long durability is provided.

According to an aspect of the present embodiments, there is provided a condensed-cyclic compound represented by Formula 1 below:

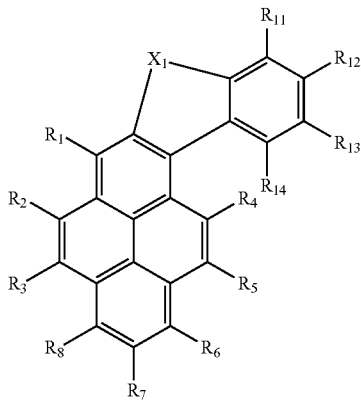

Formula 1 where $R_8$ and $R_7$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_1)_a$—$Ar_{11}$, and a group represented by —$N[—(Ar_2)_b—Ar_{12}][—(Ar_3)_c—Ar_{13}]$; or $R_8$ is connected to * of Formula 2 represented by

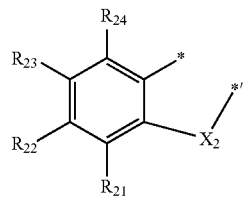

and $R_7$ is connected to *' of Formula 2; $R_1$ through $R_6$, $R_{11}$ through $R_{14}$, and $R_{21}$ through $R_{24}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_4)_d$—$Ar_{14}$, and a group represented by —$N[—(Ar_5)_e—Ar_{15}][—(Ar_6)_f—Ar_{16}]$; $Ar_1$ through $Ar_6$ are each independently selected from the group consisting of a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and a substituted or unsubstituted $C_4$-$C_{30}$ heteroarylene group; $Ar_{11}$ through $Ar_{16}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group; a through f are each independently an integer from 0 to 10; a $Ar_1$s in the group represented by —$(Ar_1)_a$—$Ar_{11}$ are identical to or different from each other, b $Ar_2$s in the group represented by —$(Ar_2)_b$—$Ar_{12}$ are identical to or different from each other, c $Ar_3$s in the group represented by —$(Ar_3)_c$—$Ar_{13}$ are identical to or different from each other, d $Ar_4$s in the group represented by —$(Ar_4)_d$—$Ar_{14}$ are identical to or different from each other, e $Ar_5$s in the group represented by —$(Ar_5)_e$—$Ar_{15}$ are identical to or different from each other, and f $Ar_6$s in the group represented by [—$(Ar_6)_f$—$Ar_{16}$] are identical to or different from each other; $X_1$ and $X_2$ are each independently a divalent linking group selected from the group consisting of —$C(Q_1)(Q_2)$- and —$N(Q_3)$-; and $Q_1$ through $Q_3$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group.

$R_1$ through $R_3$ and $R_4$ through $R_7$ may be hydrogen; $R_8$ may be selected from the group consisting of hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_1)_a$—$Ar_{11}$, and a group represented by —$N[$—$(Ar_2)_b$—$Ar_{12}][$—$(Ar_3)_c$—$Ar_{13}]$; $R_{11}$ through $R_{14}$ may be each independently selected from the group consisting of hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_4)_d$—$Ar_{14}$, and a group represented by —$N[$—$(Ar_5)_e$—$Ar_{15}][$—$(Ar_6)_f$—$Ar_{16}]$; $Ar_1$ through $Ar_6$ may be each independently selected from the group consisting of a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and a substituted or unsubstituted $C_4$-$C_{30}$ heteroarylene group; and $Ar_{11}$ and $Ar_{16}$ may be each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group.

BRIEF DESCRIPTION OF THE DRAWING

The above and other features and advantages of the present embodiments will become more apparent by describing in detail exemplary embodiments thereof with reference to the attached drawing in which:

FIG. 1 is a diagram schematically illustrating a structure of an organic light emitting diode (OLED) according to an embodiment.

DETAILED DESCRIPTION OF CERTAIN INVENTIVE EMBODIMENTS

Hereinafter, the present embodiments will be described more fully with reference to the accompanying drawings, in which exemplary embodiments are shown.

A condensed-cyclic compound represented by Formula 1 below is provided:

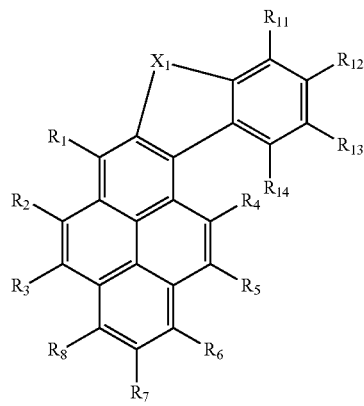

Formula 1

In Formula 1, $R_8$ and $R_7$ may be each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_1)_a$—$Ar_{11}$, and a group represented by —$N[$—$(Ar_2)_b$—$Ar_{12}][$—$(Ar_3)_c$—$Ar_{13}]$; or $R_8$ may be connected to * of Formula 2 represented by

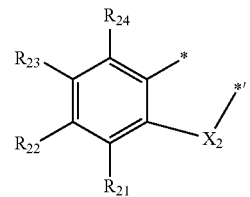

and $R_7$ may be connected to *' of Formula 2; and $R_1$ through $R_6$, $R_{11}$ through $R_{14}$, and $R_{21}$ through $R_{24}$ may be each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_4)_d$—$Ar_{14}$, and a group represented by —$N[$—$(Ar_5)_e$—$Ar_{15}][$—$(Ar_6)_f$—$Ar_{16}]$.

For example, in Formula 1, $R_5$ and $R_7$ may be each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_1)_a$—$Ar_{11}$, and a group represented by —$N[$—$(Ar_2)_b$—$Ar_{12}][$—$(Ar_3)_c$—$Ar_{13}]$, and $R_1$ through $R_6$ and $R_{11}$ through $R_{14}$ may be each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_4)_d$—$Ar_{14}$, and a group represented by —$N[$—$(Ar_5)_e$—$Ar_{15}][$—$(Ar_6)_f$—$Ar_{16}]$.

For example, in Formula 1, $R_1$ through $R_3$ and $R_4$ through $R_7$ may be hydrogen; $R_8$ may be selected from the group consisting of hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_1)_a$—$Ar_{11}$, and a group represented by —N[—$(Ar_2)_b$—$Ar_{12}$][—$(Ar_3)_c$—$Ar_{13}$]; $R_{11}$ through $R_{14}$ may be each independently selected from the group consisting of hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_4)_d$—$Ar_{14}$, and a group represented by —N[—$(Ar_5)_e$—$Ar_{15}$][—$(Ar_6)_f$—$Ar_{16}$].

$Ar_1$ through $Ar_6$ may be each independently selected from the group consisting of a substituted or unsubstituted $C_1$-$C_{30}$ alkylene group, a substituted or unsubstituted $C_2$-$C_{30}$ alkenylene group, an unsubstituted $C_5$-$C_{30}$ arylene group, and a substituted or unsubstituted $C_4$-$C_{30}$ heteroarylene group.

For example, $Ar_1$ through $Ar_6$ may be each independently selected from the group consisting of a substituted or unsubstituted $C_1$-$C_{10}$ alkylene group, a substituted or unsubstituted $C_2$-$C_{10}$ alkenylene group, a substituted or unsubstituted $C_5$-$C_{14}$ arylene group, and a substituted or unsubstituted $C_4$-$C_{14}$ heteroarylene group.

$Ar_1$ through $Ar_6$ may be each independently selected from the group consisting of a substituted or unsubstituted ethylene group, a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylenylene group, a substituted or unsubstituted chrysenylene group, a substituted or unsubstituted naphthacenylene group, a substituted or unsubstituted phenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzimidazolylene group, and a substituted or unsubstituted isoxazolylene group, but are not limited thereto.

$Ar_{11}$ through $Ar_{16}$ may be each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group.

$Ar_{11}$ through $Ar_{16}$ may be each independently selected from the group consisting of a substituted or unsubstituted $C_1$-$C_{10}$ alkyl group, a substituted or unsubstituted $C_1$-$C_{10}$ alkoxy group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenantlenyl group, a substituted or unsubstituted anthracenyl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentacenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted furinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranylene group, a substituted or unsubstituted chromenyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzimidazolyl group, and a substituted or unsubstituted isoxazolyl group, but are not limited thereto.

For example, $Ar_1$ through $Ar_6$ may be each independently selected from the group consisting of a pyridinylene group, a quinolinylene group, a benzimidazolylene group, an imidazopyridinylene group, an imidazopyrimidinylene group, a phenylene group, a $C_1$-$C_{10}$ alkyl phenylene group, a carbazolylene group, a phenylcarbazolylene group, a fluorenylene group, a $C_1$-$C_{10}$ alkyl fluorenylene group, a di($C_1$-$C_{10}$ alkyl)

fluorenylene group, an ethylene group, and a naphthylene group, but are not limited thereto.

Also, for example, $Ar_{11}$ through $Ar_{16}$ may be each independently selected from the group consisting of a methyl group, an ethyl group, a propyl group, a butyl group, a methoxy group, an ethoxy group, a propoxy group, a butoxy group, a pyridinyl group, a quinolinyl group, a benzimidazolyl group, an imidazopyridinyl group, an imidazopyrimidinyl group, a phenyl group, a carbazolyl group, a fluorenyl group, a di($C_1$-$C_{10}$ alkyl)fluorenyl group, a naphthyl group, and a functional group represented by the formula

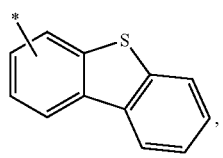

but are not limited thereto.

$R_8$ and $R_{11}$ through $R_{14}$ may be each independently selected from the group consisting of functional groups represented by Formulae 3A through 3O below, but are not limited thereto:

Formula 3A

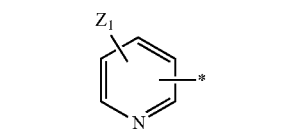

Formula 3B

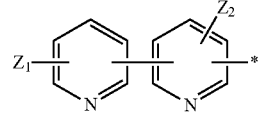

Formula 3C

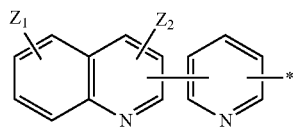

Formula 3D

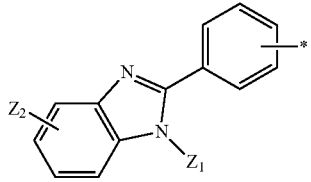

Formula 3E

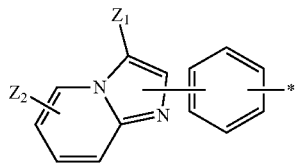

Formula 3F

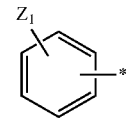

-continued

Formula 3G

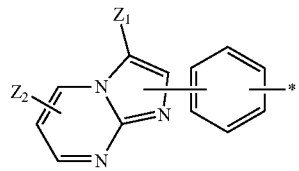

Formula 3H

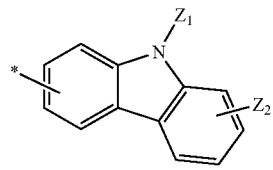

Formula 3I

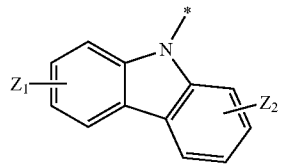

Formula 3J

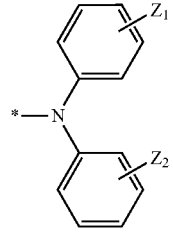

Formula 3K

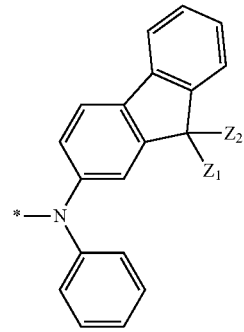

Formula 3L

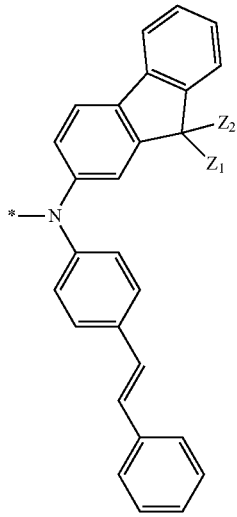

-continued

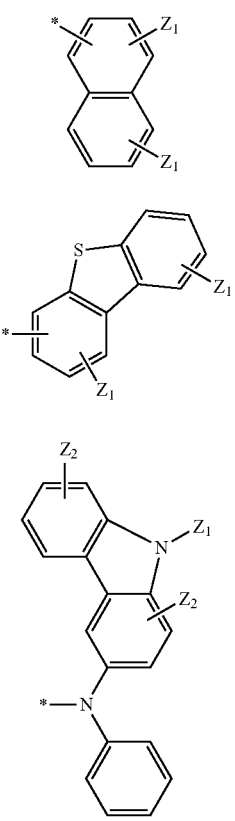

Formula 3M

Formula 3N

Formula 3O

In Formulae 3A through 3O, $Z_1$ and $Z_2$ are each independently selected from the group consisting of hydrogen, a hydroxyl group, a methyl group, an ethyl group, a propyl group, a butyl group, a methoxy group, an ethoxy group, a propoxy group, a butoxy group, a phenyl group, and a naphthyl group.

$R_8$ and $R_{11}$ through $R_{14}$ may be each independently selected from the group consisting of compounds represented by Formulae 4A through 4R below, but are not limited thereto:

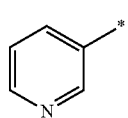

Formula 4A

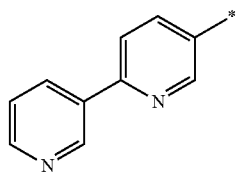

Formula 4B

Formula 4C

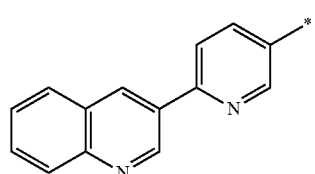

Formula 4D

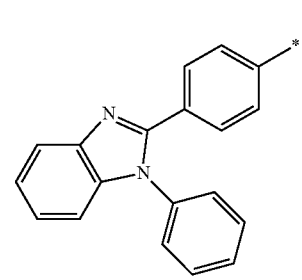

Formula 4E

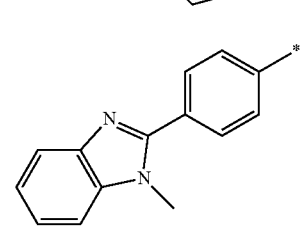

Formula 4F

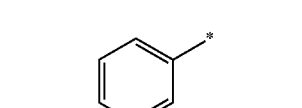

Formula 4G

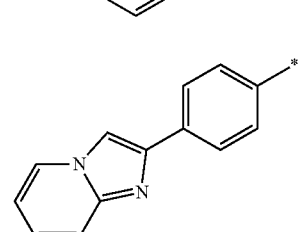

Formula 4H

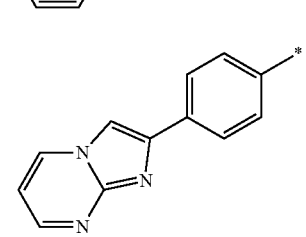

Formula 4I

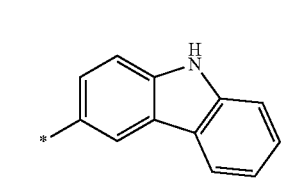

Formula 4J

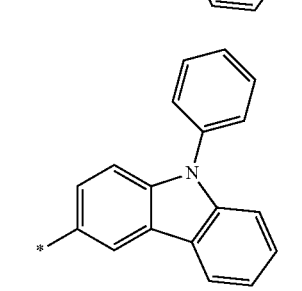

Formula 4K

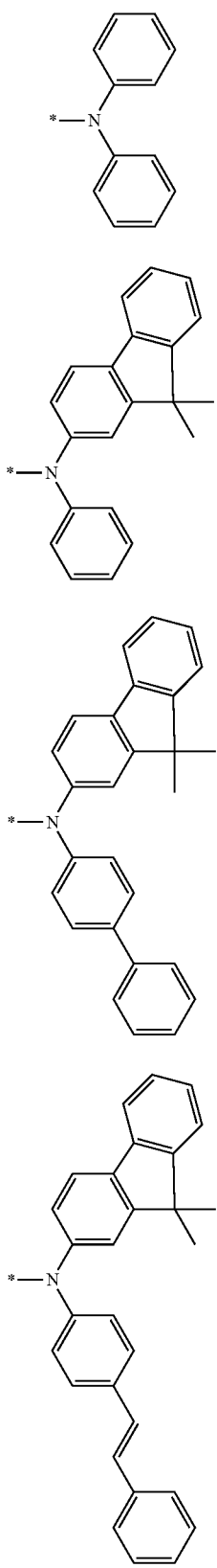

Formula 4L

Formula 4M

Formula 4N

Formula 4O

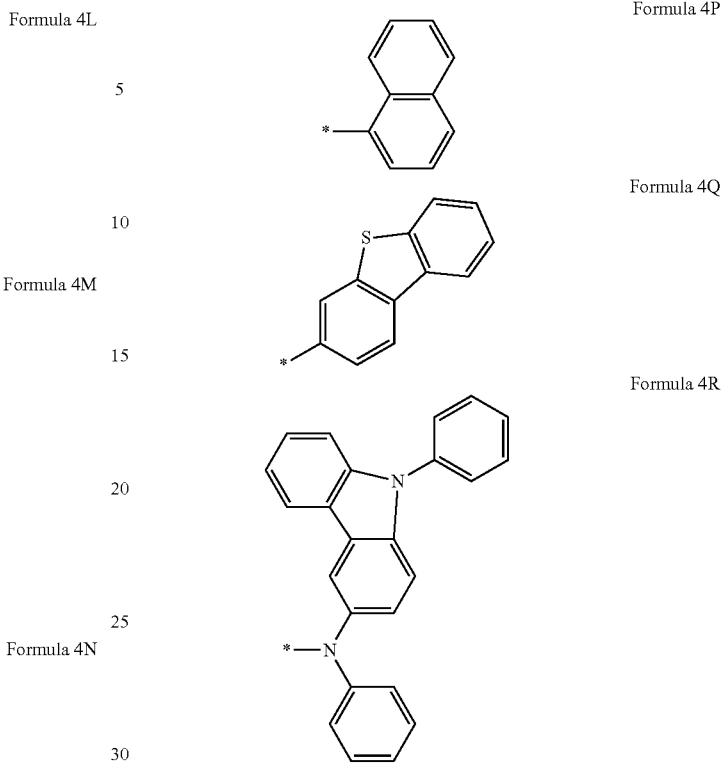

Formula 4P

Formula 4Q

Formula 4R

In Formula 1, a through f may be each independently an integer from 0 to 10. For example, a through f may be each independently 0, 1, or 2, but are not limited thereto.

In Formula 1, a $Ar_1$s in the group represented by $—(Ar_1)_a—Ar_{11}$ may be identical to or different from each other, b $Ar_2$s in the group represented by $—(Ar_2)_b—Ar_{12}$ may be identical to or different from each other, c $Ar_3$s in the group represented by $—(Ar_3)_c—Ar_{13}$ may be identical to or different from each other, d $Ar_4$s in the group represented by $—(Ar_4)_d—Ar_{14}$ may be identical to or different from each other, e $Ar_5$s in the group represented by $—(Ar_5)_e—Ar_{15}$ may be identical to or different from each other, and f $Ar_6$s in the group represented by $[—(Ar_6)_f—Ar_{16}]$ may be identical to or different from each other.

For example, in the group represented by $—(Ar_1)_a—Ar_{11}$, when a is 2, the two $Ar_1$s may be both phenylene groups, or one of the two may be a phenylene group and the other may be a benzimidazolylene group.

In Formula 1, $Q_1$ through $Q_3$ may be each independently selected from the group consisting of hydrogen, a $C_1$-$C_{30}$ alkyl group, a $C_1$-$C_{30}$ alkoxy group, a $C_5$-$C_{14}$ aryl group, and a $C_4$-$C_{14}$ heteroaryl group. For example, $Q_1$ through $Q_3$ may be each independently selected from the group consisting of hydrogen, a methyl group, an ethyl group, a propyl group, a butyl group, a methoxy group, an ethoxy group, a propoxy group, a butoxy group, a phenyl group, and a naphthyl group, but are not limited thereto. For example, $Q_1$ through $Q_3$ may be each independently hydrogen, a methyl group, or a phenyl group.

In Formula 1, $X_1$ may be selected from the group consisting of $—CH_2—$, $—CH(CH_3)—$, $—C(CH_3)_2—$, $—CH(Ph)-$, $—NH—$, and $—N(Ph)-$, wherein Ph denotes a phenyl group, but is not limited thereto.

Accordingly, the condensed-cyclic compound of Formula 1 has high thermal stability. Also, since the condensed-cyclic compound has a wide band gap, the condensed-cyclic compound may be used for various layers, such as a hole transport layer (HTL), an emissive layer (EML), and/or an electron transport layer (ETL), of an organic light emitting diode (OLED), according to substituents, such as $R_8$ and $R_{11}$ through $R_{14}$.

In Formula 1, $R_8$ may be connected to * of Formula 2 below and $R_7$ may be connected to *' of Formula 2.

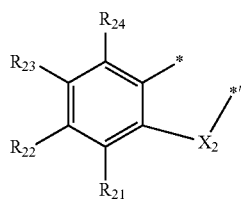

Formula 2

Accordingly, the condensed-cyclic compound represented by Formula 1 may be represented by Formula 1A below:

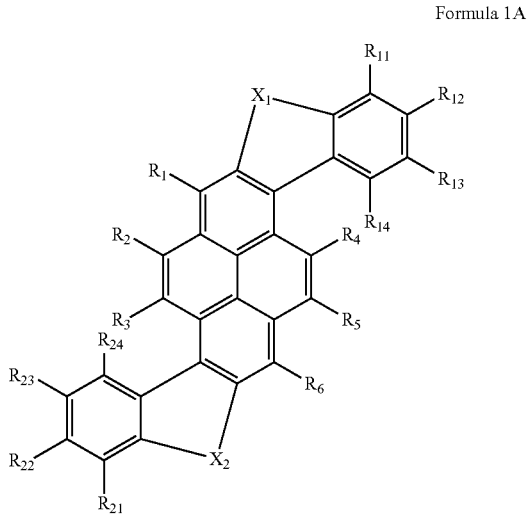

Formula 1A

In Formula 1A, $R_1$ through $R_6$ and $R_{11}$ through $R_{14}$ are as described above, and $R_{21}$ through $R_{24}$ are as described in connection with $R_{11}$ through $R_{14}$.

For example, in Formula 1A, $R_1$ through $R_6$ may be hydrogen; $R_{11}$ through $R_{14}$ and $R_{21}$ through $R_{24}$ may each independently hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_4)_d$—$Ar_{14}$, and a group represented by —N[—$(Ar_5)_e$—$Ar_{15}$][—$(Ar_6)_f$—$Ar_{16}$].

Here, $Ar_4$ through $Ar_6$, $A_{14}$ through $Ar_{16}$, and d through f are as described above.

In Formula 1A, $R_{11}$ through $R_{14}$ and $R_{21}$ through $R_{24}$ may be each independently selected from the group consisting of the compounds represented by Formulae 3A through 3O, but are not limited thereto.

In Formula 1A, $R_{11}$ through $R_{14}$ and $R_{21}$ through $R_{24}$ may be each independently selected from the group consisting of the functional groups represented by Formulae 4A through 4R, but are not limited thereto.

In Formula 1A, $Q_1$ through $Q_3$ and $X_1$ are as described above, and $X_2$ is as described above in connection with $X_1$.

Since the condensed-cyclic compound of Formula 1 may be represented by Formula 1A, the condensed-cyclic compound has high thermal stability. Also, since the condensed-cyclic compound has a wide band gap, the condensed-cyclic compound may be used for various layers, such as a HTL, an EML, and/or an ETL, of an OLED, according to substituents, such as $R_8$ and $R_{11}$ through $R_{14}$.

According to an embodiment, in Formula 1, $R_1$ through $R_3$ and $R_4$ through $R_7$ may be hydrogen; $R_8$ and $R_{11}$ through $R_{14}$ may be each independently selected from the group consisting of hydrogen and functional groups represented by Formulae 3A through 3O; and $X_1$ may be a divalent linking group selected from the group consisting of —C($Q_1$)($Q_2$)- and —N($Q_3$)-, wherein $Q_1$ through $Q_3$ may be each independently selected from the group consisting of hydrogen, a methyl group, an ethyl group, a propyl group, a butyl group, a methoxy group, an ethoxy group, a propoxy group, a butoxy group, a phenyl group, and a naphthyl group.

According to another embodiment, in Formula 1, $R_1$ through $R_3$, $R_4$ through $R_7$, $R_{11}$, $R_{13}$, and $R_{14}$ may be hydrogen; $R_8$ and $R_{12}$ may be each independently selected from the group consisting of hydrogen and the functional groups represented by Formulae 3A through 3O; and $X_1$ may be a divalent linking group selected from the group consisting of —C($Q_1$)($Q_2$)- and —N($Q_3$)-, wherein $Q_1$ through $Q_3$ may be each independently selected from the group consisting of hydrogen, a methyl group, an ethyl group, a propyl group, a butyl group, a methoxy group, an ethoxy group, a propoxy group, a butoxy group, a phenyl group, and a naphthyl group.

According to another embodiment, in Formula 1, $R_1$ through $R_3$, $R_4$ through $R_7$, $R_{11}$, $R_{13}$, and $R_{14}$ may be hydrogen; $R_8$ and $R_{12}$ may be each independently selected from the group consisting of hydrogen and the functional groups represented by Formulae 4A through 4R; and $X_1$ may be selected from the group consisting of —$CH_2$—, —CH($CH_3$)—, —C($CH_3$)$_2$—, —CH(Ph)-, —NH—, and —N(Ph)-, wherein Ph denotes a phenyl group.

According to another embodiment, in Formula 1, $R_1$ through $R_3$, $R_4$ through $R_7$, $R_{11}$, $R_{13}$, and $R_{14}$ may be hydrogen; $R_8$ and $R_{12}$ may be each independently selected from the group consisting of hydrogen and the functional groups represented by Formulae 4A through 4R; and $X_1$ may be selected from the group consisting of —$CH_2$—, —CH($CH_3$)—, —C($CH_3$)$_2$—, and —CH(Ph)-, wherein Ph denotes a phenyl group.

According to an embodiment, in Formula 1, $R_8$ may be connected to * of Formula 2, $R_7$ may be connected to *' of Formula 2 (that is, Formula 1 is represented by Formula 1A), $R_1$ through $R_6$ may be hydrogen; $R_{11}$ through $R_{14}$ and $R_{21}$ through $R_{24}$ may be each independently selected from the group consisting of hydrogen and the functional groups represented by Formulae 3A through 3O; and $X_1$ and $X_2$ may be each independently a divalent linking group selected from the group consisting of —C($Q_1$)($Q_2$)- and —N($Q_3$)-, wherein $Q_1$ through $Q_3$ may be each independently selected form the group consisting of hydrogen, a methyl group, an ethyl group, a propyl group, a butyl group, a methoxy group, an ethoxy group, a propoxy group, a butoxy group, a phenyl group, and a naphthyl group.

According to another embodiment, in Formula 1, $R_8$ may be connected to * of Formula 2, $R_7$ may be connected to *' of Formula 2 (that is, Formula 1 is represented by Formula 1A), $R_1$ through $R_6$, $R_{11}$, $R_{13}$, $R_{14}$, $R_{21}$, $R_{23}$, and $R_{24}$ may be hydrogen; $R_{12}$ and $R_{22}$ may be each independently selected from the group consisting of hydrogen and the functional groups represented by Formulae 3A through 3O; and $X_1$ and $X_2$ may be each independently a divalent linking group selected from the group consisting of —C(Q₁)(Q₂)- and —N(Q₃)-, wherein $Q_1$ through $Q_3$ may be each independently selected from the group consisting of hydrogen, a methyl group, an ethyl group, a propyl group, a butyl group, a methoxy group, an ethoxy group, a propoxy group, a butoxy group, a phenyl group, and a naphthyl group.

According to another embodiment, in Formula 1, $R_8$ may be connected to * of Formula 2, $R_7$ may be connected to *' of Formula 2 (that is, Formula 1 is represented by Formula 1A); $R_1$ through $R_6$, $R_{11}$, $R_{13}$, $R_{14}$, $R_{21}$, $R_{23}$, and $R_{24}$ may be hydrogen; $R_{12}$ and $R_{22}$ may be each independently selected from the group consisting of hydrogen and the functional groups represented by Formulae 4A through 4R; and $X_1$ and $X_2$ may be each independently selected from the group consisting of —CH₂—, —CH(CH₃)—, —C(CH₃)₂—, —CH(Ph)-, —NH—, and —N(Ph)-, wherein Ph denotes a phenyl group.

According to another embodiment, in Formula 1, $R_8$ may be connected to * of Formula 2, $R_7$ may be connected to *' of Formula 2 (that is, Formula 1 is represented by Formula 1A); $R_1$ through $R_6$, $R_{11}$, $R_{13}$, $R_{14}$, $R_{21}$, $R_{23}$, and $R_{24}$ are hydrogen; $R_{12}$ and $R_{22}$ may be each independently selected from the group consisting of hydrogen and the functional groups represented by Formulae 4A through 4R; and $X_1$ and $X_2$ may be each independently selected from the group consisting of —CH₂—, —CH(CH₃)—, —C(CH₃)₂—, and —CH(Ph)-.

According to another embodiment, the condensed-cyclic compound represented by Formula 1 may be one of Compounds 1 to 43 below, but is not limited thereto.

Compound 1

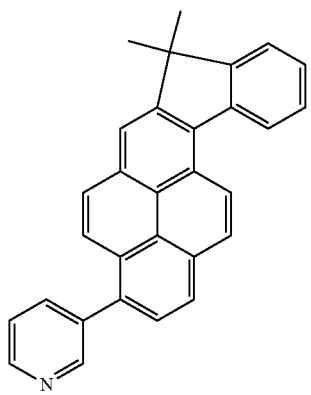

Compound 2

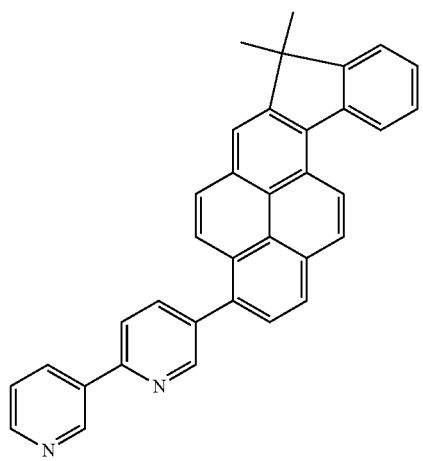

Compound 3

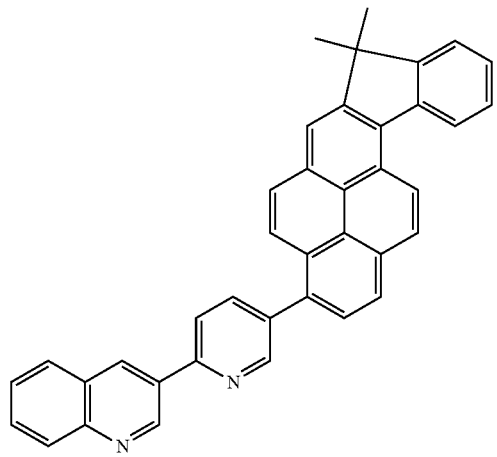

Compound 4

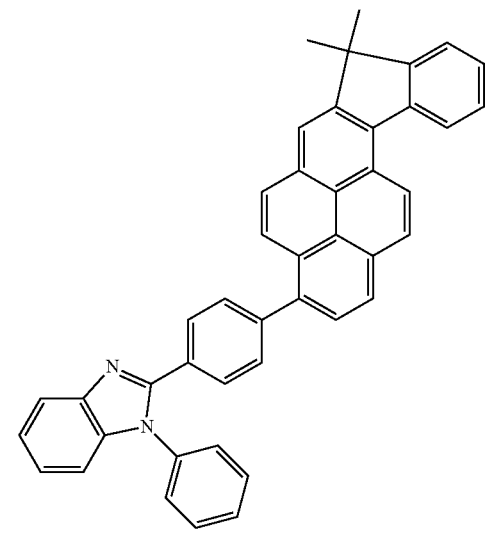

Compound 5

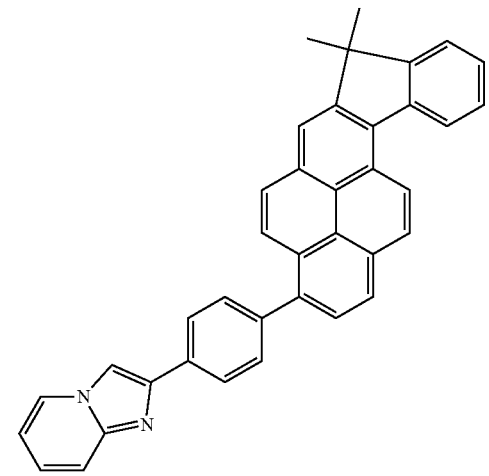

Compound 6
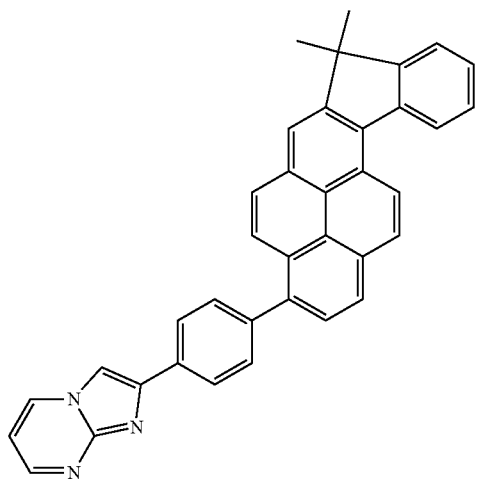
Compound 7
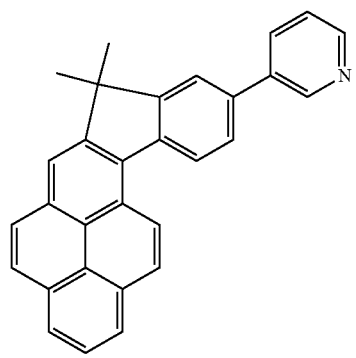
Compound 8
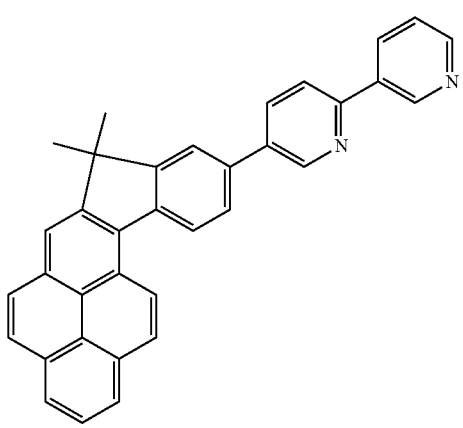
Compound 9
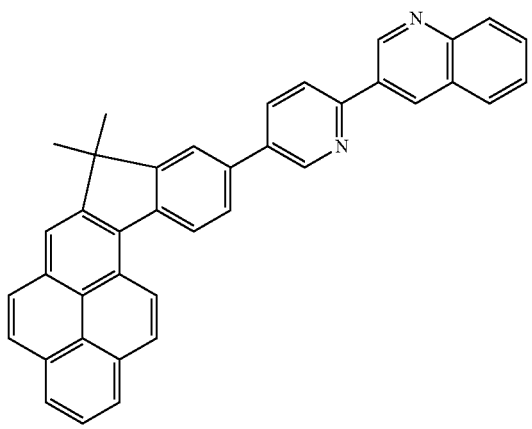
Compound 10
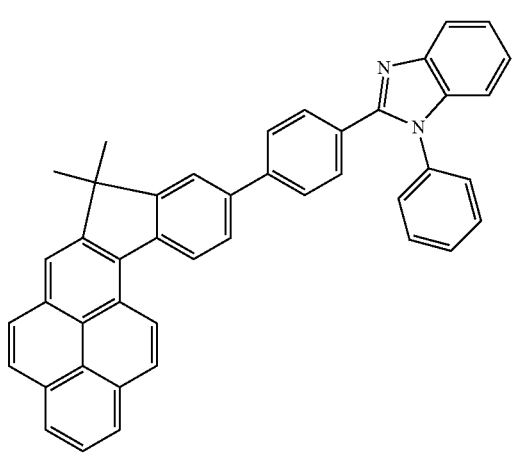
Compound 11
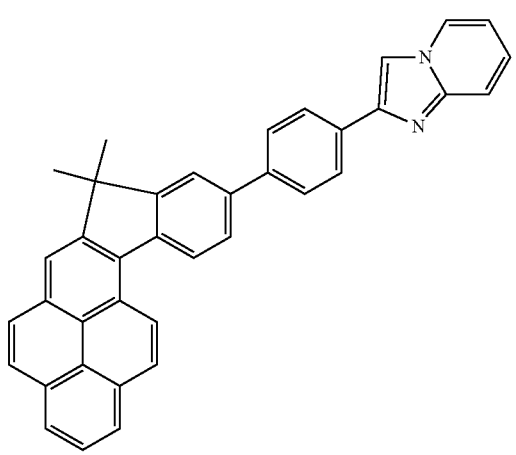

-continued
Compound 12
Compound 13
Compound 14
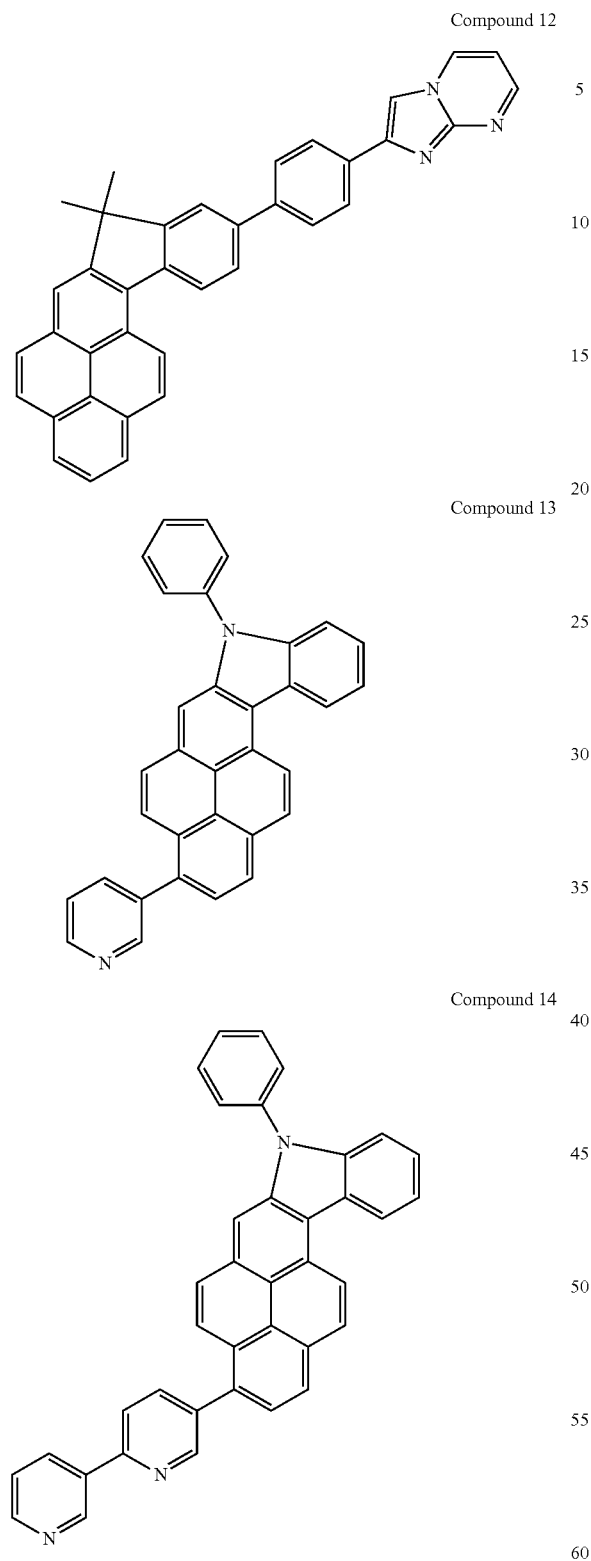
-continued
Compound 15
Compound 16
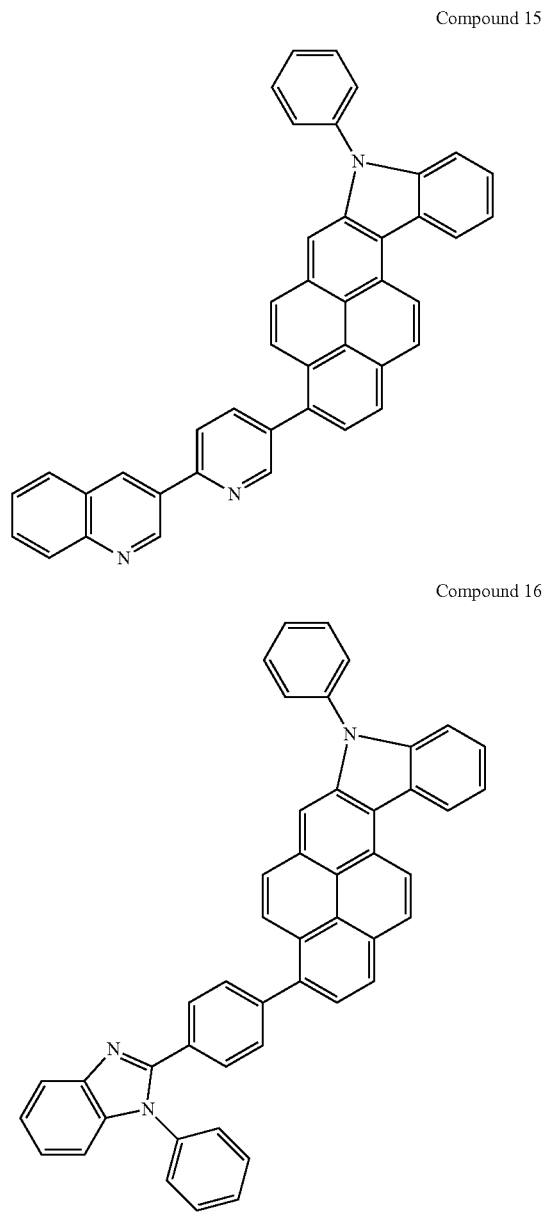

Compound 17
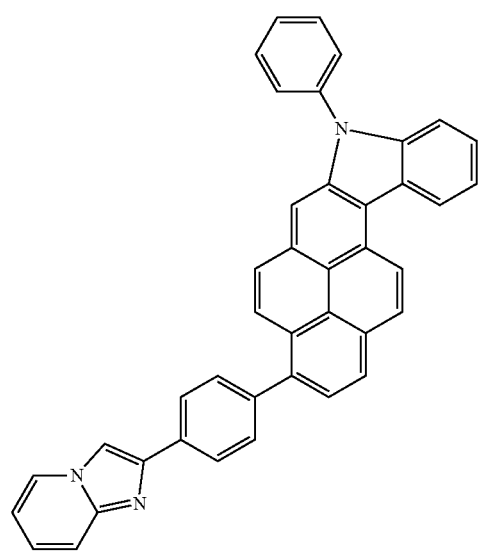
Compound 20
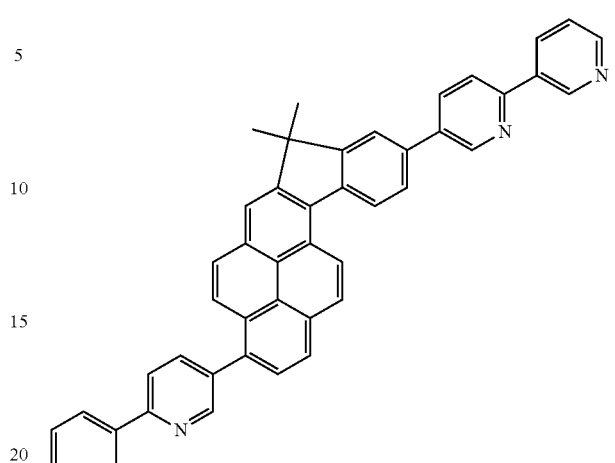
Compound 18
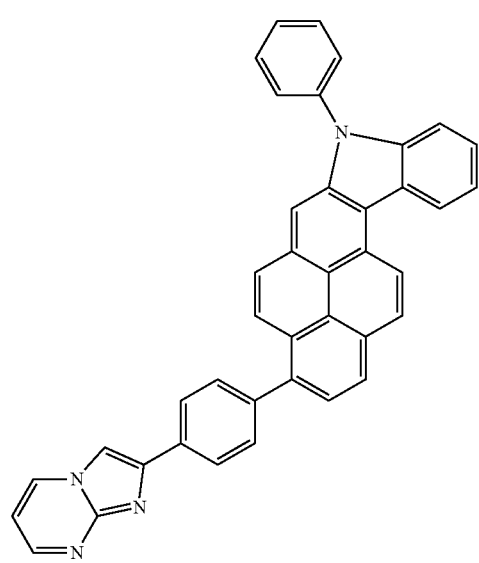
Compound 21
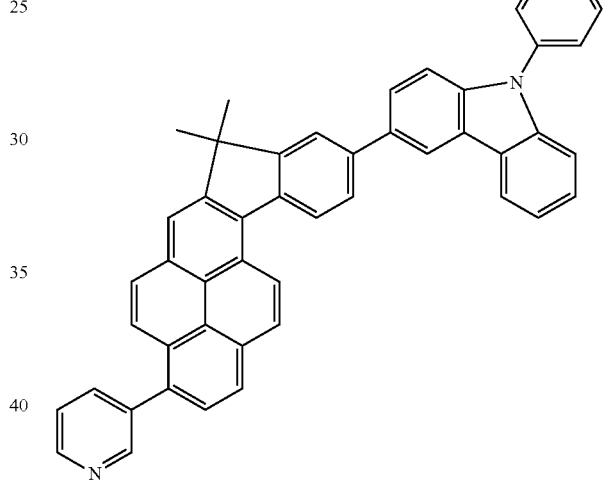
Compound 19
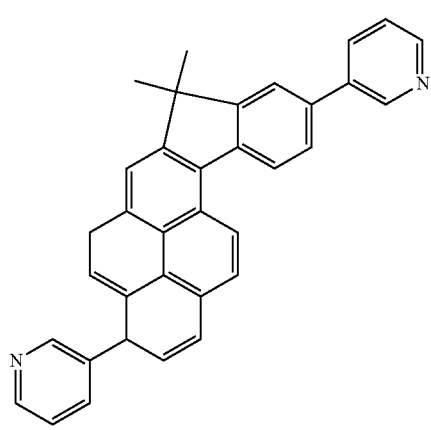
Compound 22
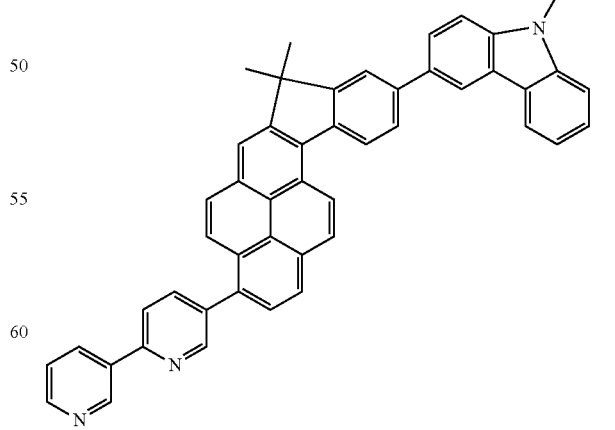

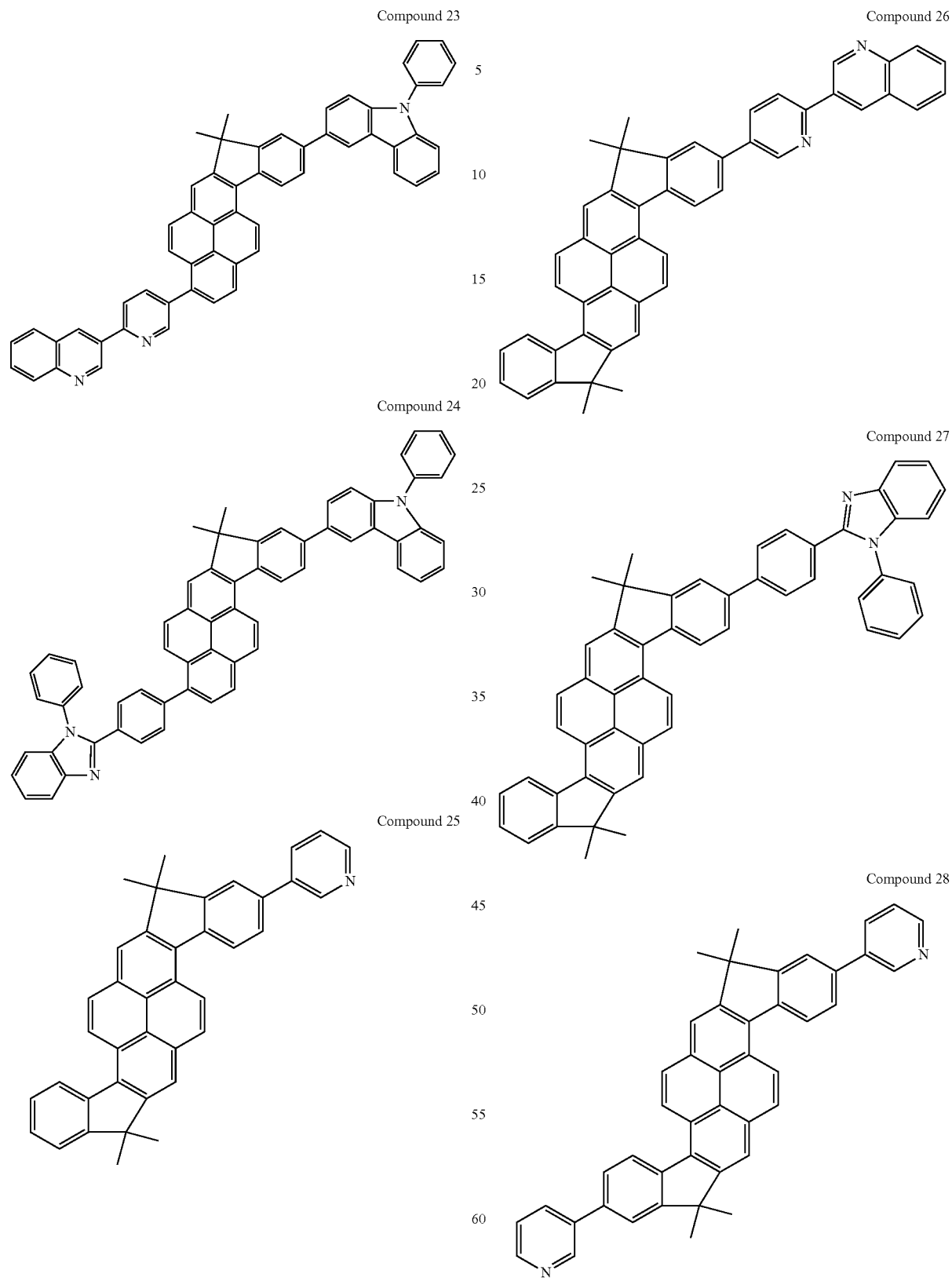

-continued
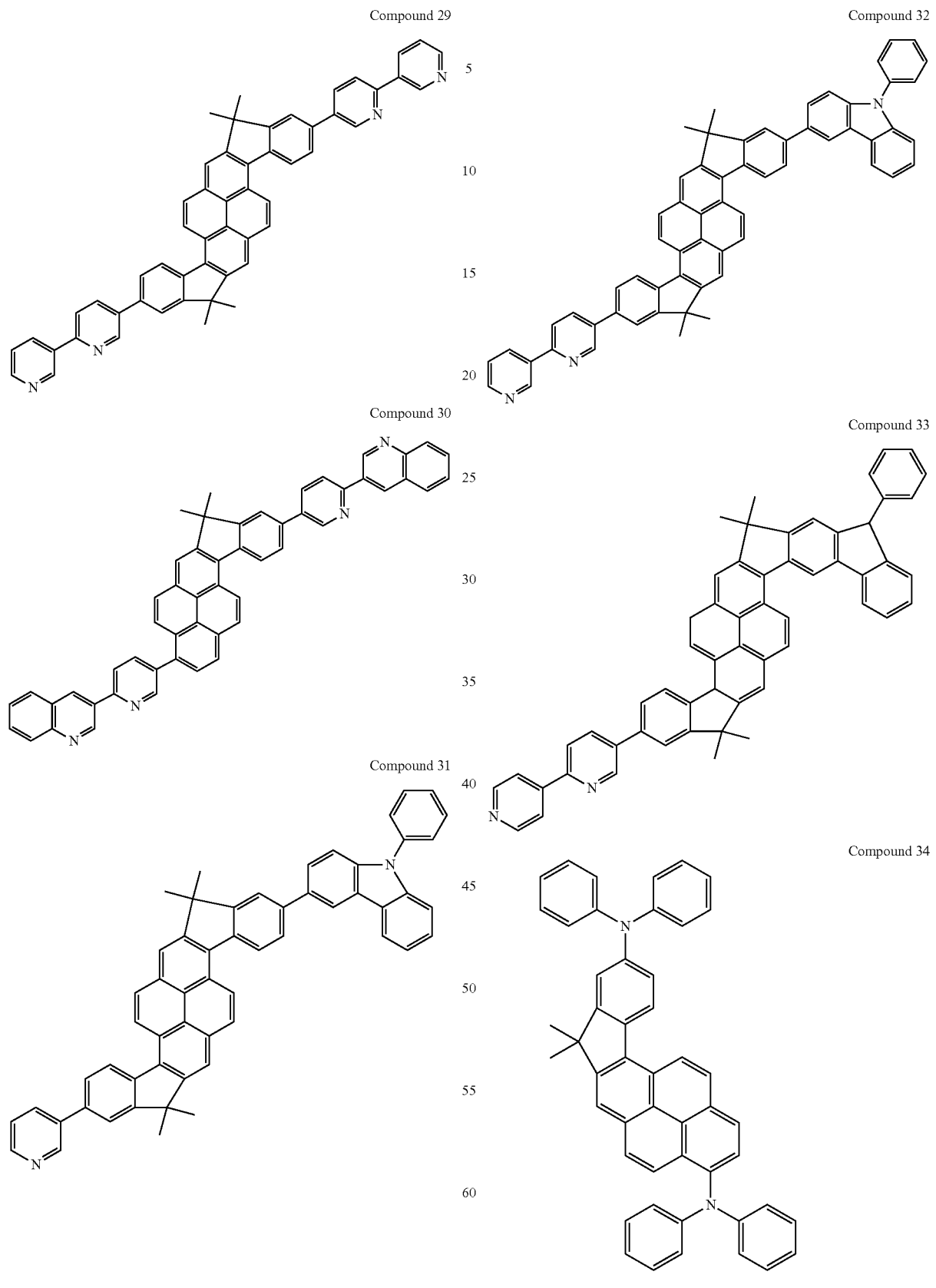

Compound 35
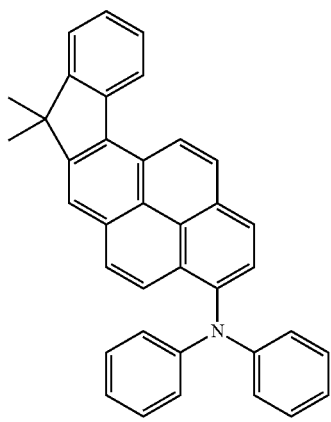
Compound 36
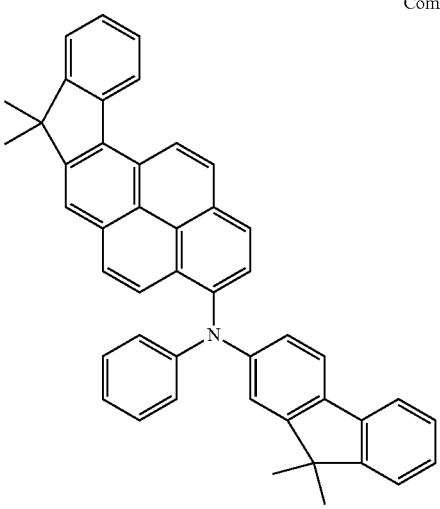
Compound 37
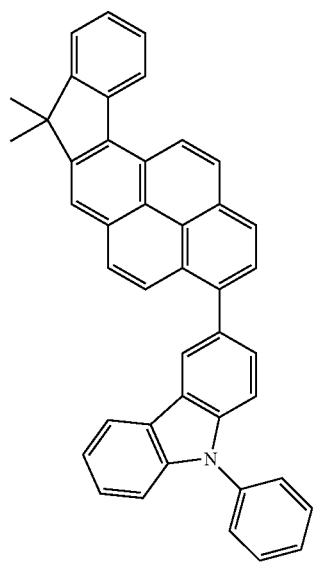
Compound 38
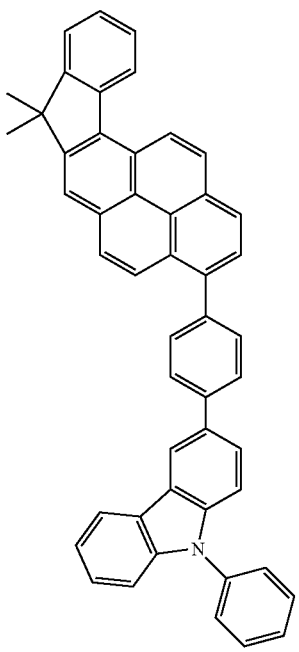
Compound 39
Compound 40
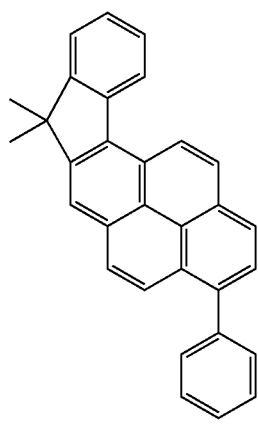

-continued

Compound 41

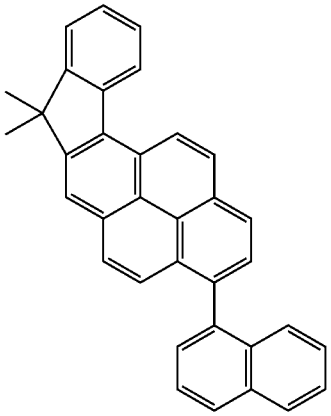

Compound 42

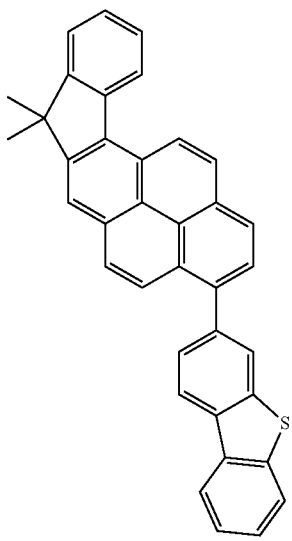

Compound 43

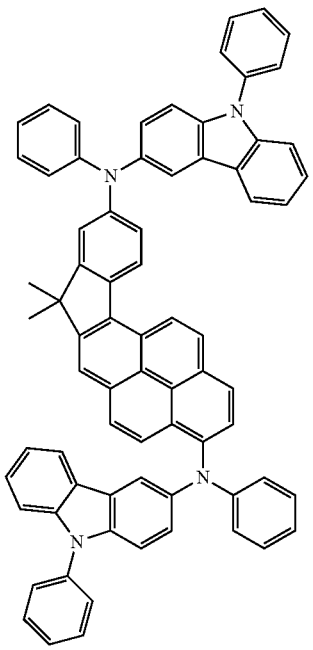

Examples of the unsubstituted $C_1$-$C_{30}$ alkyl group or the $C_1$-$C_{30}$ alkyl group used herein include methyl, ethyl, propyl, isobutyl, sec-butyl, pentyl, iso-amyl, hexyl, and the like. In the substituted $C_1$-$C_{30}$ alkyl group, at least one hydrogen atom of the unsubstituted $C_1$-$C_{30}$ alkyl group may be substituted with a halogen atom, a hydroxyl group, a nitro group, a cyano group, an amino group, an amidino group, hydrazine, hydrazone, a carboxyl group or salts thereof, a sulfonic acid group or salts thereof, a phosphoric acid or salts thereof, a $C_1$-$C_{30}$ alkyl group, a $C_1$-$C_{30}$ alkenyl group, a $C_1$-$C_{30}$ alkynyl group, a $C_6$-$C_{30}$ aryl group, or a $C_2$-$C_{20}$ heteroaryl group. The substituted or unsubstituted $C_1$-$C_{30}$ alkylene group has the same structure as the substituted or unsubstituted $C_1$-$C_{30}$ alkyl group as described above, but is a divalent linking group.

The unsubstituted $C_1$-$C_{30}$ alkoxy group or the $C_1$-$C_{30}$ alkoxy group may be a group represented by —OA, wherein A is the unsubstituted $C_1$-$C_{30}$ alkyl group, and examples of the unsubstituted $C_1$-$C_{30}$ alkoxy group are methoxy, ethoxy, and isopropyloxy. At least one hydrogen atom in the unsubstituted $C_1$-$C_{30}$ alkoxy group may be substituted with the substituents described with reference to the substituted $C_1$-$C_{30}$ alkyl group.

The unsubstituted $C_2$-$C_{30}$ alkenyl group or the $C_2$-$C_{30}$ alkenyl group has at least one carbon-carbon double bond in the center or at one end of the unsubstituted $C_2$-$C_{30}$ alkyl group structure. Examples of the unsubstituted alkenyl group include ethenyl, propenyl, and butenyl. At least one hydrogen atom in the unsubstituted $C_2$-$C_{30}$ alkenyl group may be substituted with the substituents described with reference to the substituted $C_1$-$C_{30}$ alkyl group. The substituted or unsubstituted $C_2$-$C_{30}$ alkenylene group has the same structure as the substituted or unsubstituted $C_2$-$C_{30}$ alkenyl group described above, but is a divalent linking group.

The unsubstituted $C_2$-$C_{30}$ alkynyl group or the $C_2$-$C_{30}$ alkynyl group has a carbon-carbon triple bond in the center or at one end of the $C_2$-$C_{30}$ alkyl group structure. Examples of the unsubstituted $C_2$-$C_{30}$ alkynyl group and acetylene, propylene, isopropylacetylene, and t-butylacetylene. At least one hydrogen atom in the alkynyl group may be substituted with the substituents described with reference to the substituted $C_1$-$C_{30}$ alkyl group.

The unsubstituted $C_5$-$C_{30}$ aryl group is a monovalent group having a carbocyclic aromatic system having 5 to 30 carbon atoms including at least one aromatic ring. The unsubstituted $C_5$-$C_{30}$ arylene group is a divalent group having a carbocyclic aromatic system having 5 to 30 carbon atoms including at least one aromatic ring. When the aryl group and the arylene group have at least two rings, the at least two rings may be fused to each other. At least one hydrogen atom in the aryl group and the arylene group may be substituted with the substituents described with reference to the substituted $C_1$-$C_{30}$ alkyl group.

Examples of the substituted or unsubstituted $C_5$-$C_{30}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted or unsubstituted $C_5$-$C_{30}$ arylene group may be easily derived from examples of the substituted or unsubstituted $C_5$-$C_{30}$ aryl group.

The unsubstituted $C_4$-$C_{30}$ heteroaryl group is a monovalent group having at least one aromatic ring having at least one of the hetero atoms selected from the group consisting of N, O, P, and S. The unsubstituted $C_2$-$C_{30}$ heteroarylene group is a divalent group having at least one aromatic ring having at least one of the hetero atoms selected from the group consisting of N, O, P, and S. In this regard, when the heteroaryl group and the heteroarylene group have at least two rings, the at least two rings may be fused with each other. At least one hydrogen atom in the heteroaryl group and the heteroarylene group may be substituted with the substituents described with reference to the substituted $C_1$-$C_{30}$ alkyl group.

Examples of the unsubstituted $C_4$-$C_{30}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzimidazolyl group, an imidazopyridinyl group and an imidazopyrimidinyl group. Examples of the substituted and unsubstituted $C_4$-$C_{30}$ heteroarylene group may be easily derived from examples of the substituted or unsubstituted $C_4$-$C_{30}$ arylene group.

The condensed-cyclic compound of Formula 1 may be synthesized using an organic synthesis method. A method of synthesizing the condensed-cyclic compound may be referred to embodiments that will be described later.

For example, Reaction Scheme 1A below is a reaction scheme for synthesizing the condensed-cyclic compound of Formula 1:

Reaction Scheme 1A

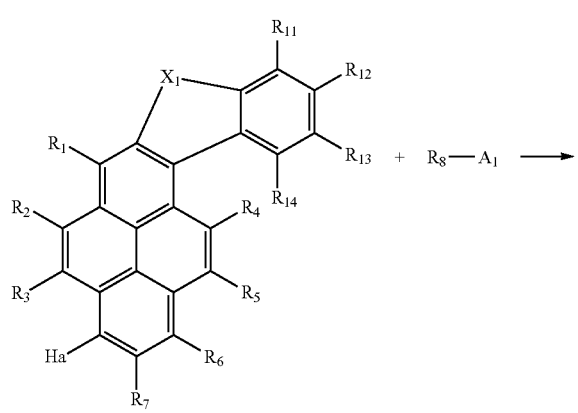

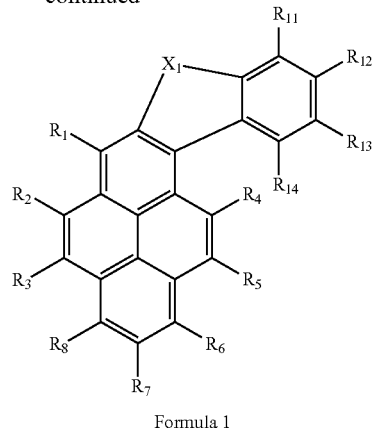

Formula 1

In Reaction Scheme 1A, R1 through R8, R11 through R14, and X1 are defined as described above.

In Reaction Scheme 1A, Ha denotes a halogen atom, and may be —F, —Cl, —Br, or —I.

In Reaction Scheme 1A, A1 may be a hydrogen atom,

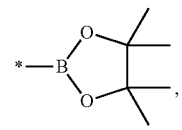

or —B(OH)2, but is not limited thereto and may be selected from well known various moiety according to selected R8.

Reaction Scheme 1A is an example of a method of synthesizing the condensed-cyclic compound of Formula 1, and one of ordinary skill in the art may synthesize the condensed-cyclic compound of Formula 1 by using a well-known organic synthesis method by referring to Reaction Scheme 1A and the structure of the compound of Formula 1.

The condensed-cyclic compound of Formula 1 may be used in an organic layer of an OLED. An embodiment provides an OLED including a first electrode, a second electrode, and an organic layer disposed between the first electrode and the second electrode, wherein the organic layer includes the condensed-cyclic compound of Formula 1 described above.

Here, the organic layer may be an EML, a HTL, or an ETL, but is not limited thereto. When the condensed-cyclic compound of Formula 1 is used as an EML, the condensed-cyclic compound may be used as a host or a dopant.

FIG. 1 is a diagram schematically illustrating a structure of an OLED 10 according to an embodiment. Hereinafter, a structure of the OLED 10 and a method of manufacturing the OLED 10 according to an embodiment will now be described with reference to FIG. 1.

The OLED 10 includes a substrate 11, a first electrode 13, an organic layer 15, and a second electrode 17, which are sequentially stacked in this order.

The substrate 11, which may be any substrate that is used in conventional OLEDs, may be a glass substrate or a transparent plastic substrate with excellent mechanical strength, thermal stability, transparency, surface smoothness, ease of handling, and waterproofness.

The first electrode 13 may be formed by depositing or sputtering a material that is used to form the first electrode 13 on the substrate. When the first electrode 13 constitutes an anode, the material used to form the first electrode 13 may be a high work-function material so as to facilitate hole injection. The first electrode 13 may be a reflective electrode or a transparent electrode. Transparent and conductive materials such as indium tin oxide (ITO), indium zinc oxide (IZO), tin dioxide (SnO2), and zinc oxide (ZnO) may be used to form the first electrode 13. Alternatively, the first electrode 13 may be formed by using magnesium (Mg), aluminum (Al), aluminum-lithium (Al—Li), calcium (Ca), magnesium-indium (Mg—In), magnesium-silver (Mg—Ag), or the like.

The organic layer 15 may be disposed on the first electrode 13. The term "organic layer" used herein indicates any layer interposed between the first electrode 13 and the second electrode 17. The organic layer 15 may not be formed of pure organic materials, and may also include a metal complex.

The organic layer 15 may include at least one of a hole injection layer (HIL), a HTL, an EML, a hole blocking layer (HBL), an ETL and an electron injection layer (EIL).

The HIL may be formed on the first electrode 13 by using a vacuum deposition method, a spin coating method, a casting method, a Langmuir-Blodgett (LB) method, or the like.

When the HIL is formed by using a vacuum deposition method, vacuum deposition conditions may vary according to a compound that is used to form the HIL, and the desired structure and thermal properties of the HIL to be formed. In general, however, the vacuum deposition method may be performed at a deposition temperature of about 100° C. to about 500° C., under a pressure of about 10-8 torr to about 10-3 torr, and at a deposition rate of about 0.01 to about 100 Å/sec.

When the HIL is formed by using a spin coating method, the coating conditions may vary according to a compound that is used to form the HIL, and the desired structure and thermal properties of the HIL to be formed. In general, however, conditions for the spin coating method may include a coating rate of about 2,000 rpm to about 5,000 rpm and a heat treatment temperature of about 80° C. to about 200° C., wherein the heat treatment is performed to remove a solvent after coating.

The HIL may be formed of any well known hole injecting material. Examples of the hole injecting material include N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4"-tris(3-methylphenylphenylamino)triphenylamine (m-MTDATA), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonicacid (Pani/CSA), and (polyaniline)/poly(4-styrenesulfonate) (PANI/PSS), but are not limited thereto.

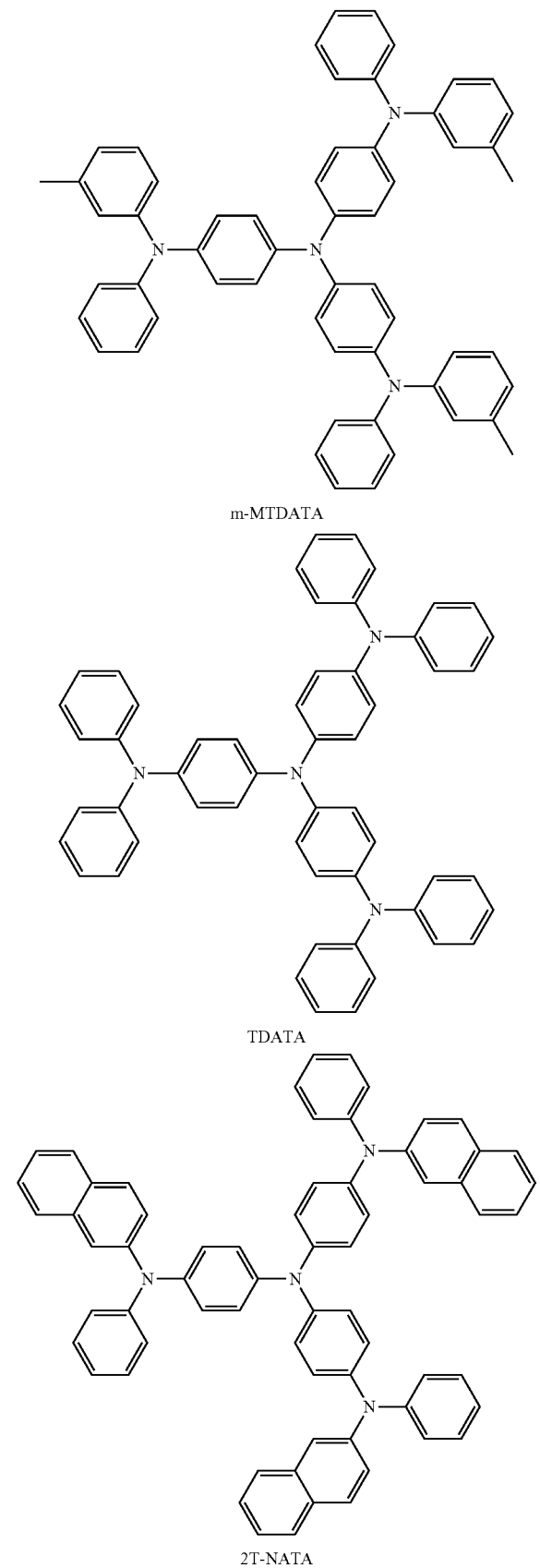

m-MTDATA

TDATA

2T-NATA

The thickness of the HIL may be about 100 Å to about 10000 Å, and for example, about 100 Å to about 1000 Å. When the thickness of the HIL is within this range, the HIL may have excellent hole injecting ability without a substantial increase in driving voltage.

Then, the HTL may be formed on the HIL by using a vacuum deposition method, a spin coating method, a casting method, a LB method, or the like. When the HTL is formed by using a vacuum deposition method or a spin coating method, the conditions for deposition and coating may be similar to those for the formation of the HIL, although the conditions for the deposition and coating may vary according to the material that is used to form the HTL.

A HTL material may include the condensed-cyclic compound of Formula 1 described above. Alternatively, the HTL may be formed of any material that is commonly used to form a HTL. Examples of the material that is used to form the HTL include: a carbazole derivative such as N-phenylcarbazole and polyvinylcarbazole; an amine derivative having an aromatic condensation ring such as N,N'-bis(3-methylphenyl)-N,N'-diphenyl-[1,1-biphenyl]-4,4'-diamine (TPD), and N,N'-di(naphthalene-1-yl)-N,N'-diphenyl benzydine (α-NPD); and a triphenylamine-based material such as 4,4',4"-tris(N-carbazolyl)triphenylamine (TCTA). Among these materials, TCTA may not only transport holes but also inhibit excitons from being diffused into the EML.

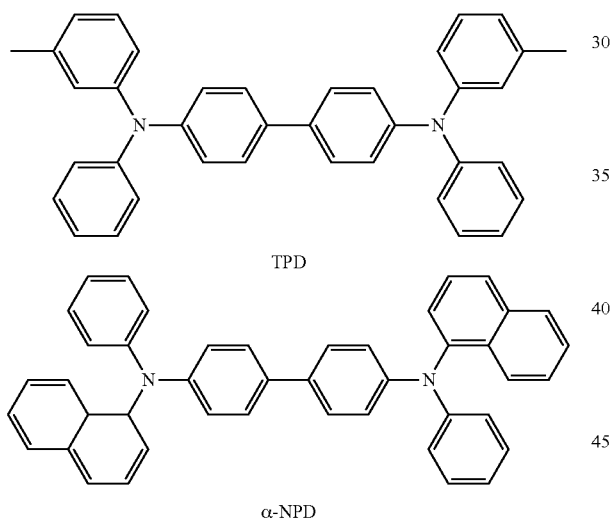

TPD

α-NPD

The thickness of the HTL may be about 50 Å to about 1000 Å, and for example, about 100 Å to about 800 Å. When the thickness of the HTL is within the range described above, the HTL may have excellent hole transporting ability without a substantial increase in driving voltage.

Then, an EML may be formed on the HTL by using a vacuum deposition method, a spin coating method, a casting method, an LB method, or the like. When the EML is formed using a vacuum deposition method or a spin coating method, the conditions for deposition and coating may be similar to those for the formation of the HIL, although the conditions for deposition and coating may vary according to the material that is used to form the EML.

The EML may include the condensed-cyclic compound represented by Formula 1 as previously described. The EML may include only the condensed-cyclic compound of Formula 1; include the condensed-cyclic compound of Formula 1 as a host and a well known dopant; or include a well known host and the condensed-cyclic compound of Formula 1 as a dopant. Examples of the well known host include $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA), but are not limited thereto.

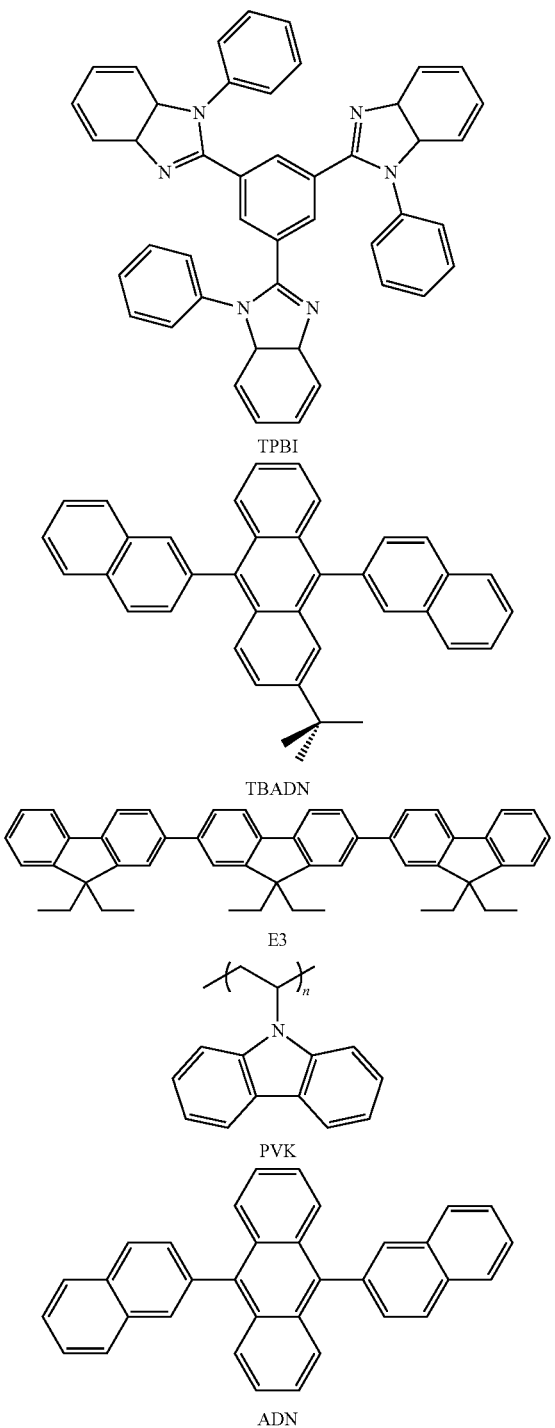

TPBI

TBADN

E3

PVK

ADN

Examples of a well known red dopant include PtOEP, $Ir(piq)_3$, and $Btp_2Ir(acac)$, but are not limited thereto.

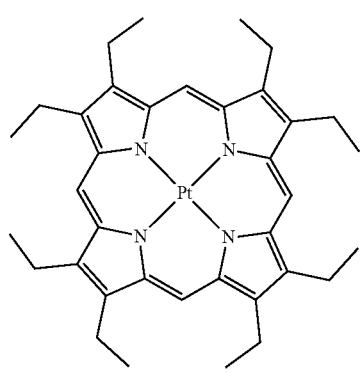

PtOEP

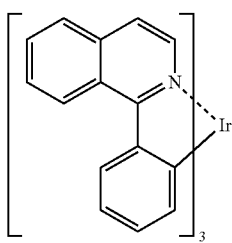

Ir(piq)₃

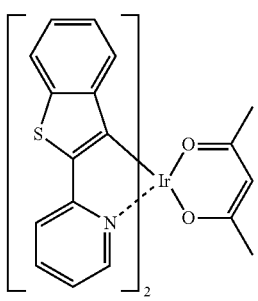

Btp₂Ir(acac)

Also, examples of well known green dopant include Ir(ppy)₃ (ppy=phenylpyridine), Ir(ppy)₂(acac), and Ir(mpyp)₃, but are not limited thereto.

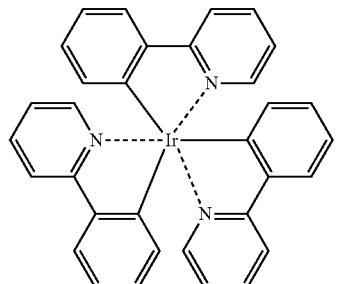

Ir(ppy)₃

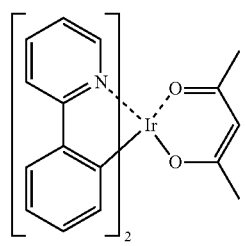

Ir(ppy)₂(acac)

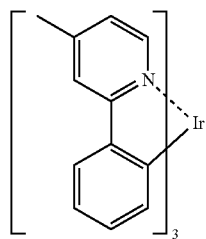

Ir(mpyp)₃

Examples of well known blue dopant include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBP), but are not limited to.

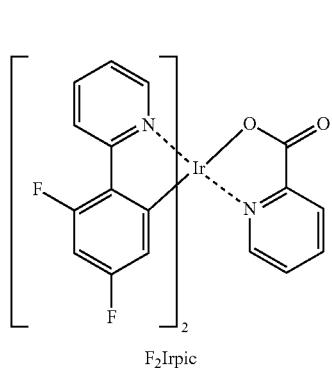

F₂Irpic

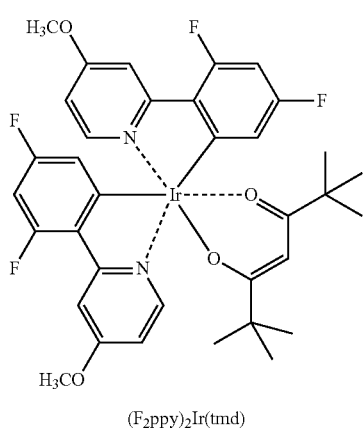

(F₂ppy)₂Ir(tmd)

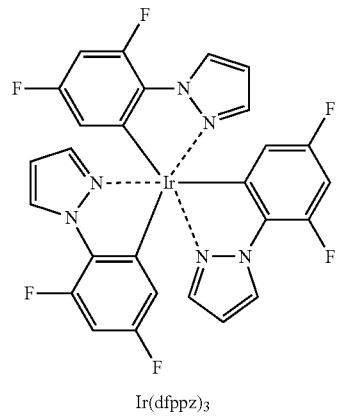

Ir(dfppz)₃

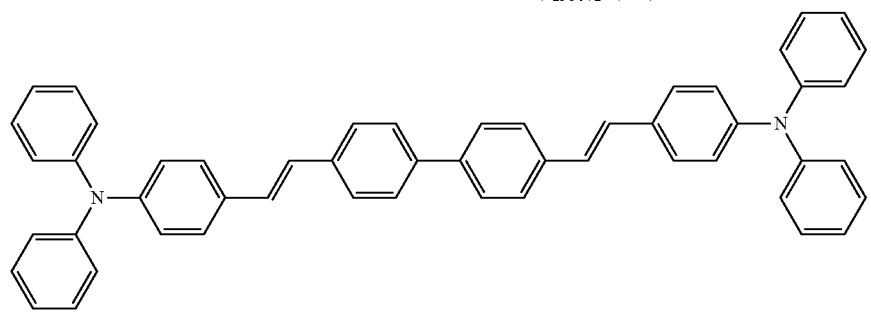

DPAVBi

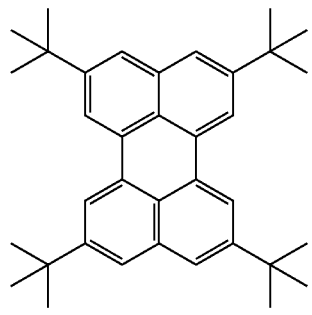

TBPe

When the EML includes a host and a dopant, an amount of the dopant may be generally in a range from about 0.01 to about 15 parts by weight based on about 100 parts by weight of the host, but is not limited thereto.

The thickness of the EML may be about 100 Å to about 1000 Å, and for example, about 200 Å to about 600 Å. When the thickness of the EML is within this range, the EML may have excellent emitting ability without a substantial increase in driving voltage.

When a phosphorescent dopant is also used to form the EML, a HBL may be formed between the HTL and the EML by using a vacuum deposition method, a spin coating method, a casting method, a LB method, or the like, in order to prevent diffusion of triplet excitons or holes into an ETL. When the HBL is formed by using a vacuum deposition method or a spin coating method, the conditions for deposition and coating may be similar to those for the formation of the HIL, although the conditions for deposition and coating may vary according to the material that is used to form the HBL. Any material that is commonly used to form a HBL may be used. Examples of materials for forming the HBL include an oxadiazole derivative, a triazole derivative, and a phenanthroline derivative, but are not limited thereto.

The thickness of the HBL may be in the range of about 50 Å to about 1000 Å, for example, about 100 Å to about 300 Å. When the thickness of the HBL is within these ranges, the HBL may have an excellent hole blocking ability without a substantial increase in driving voltage.

Then, an ETL is formed by using a vacuum deposition method, a spin coating method, a casting method, or the like. When the ETL is formed by using a vacuum deposition method or a spin coating method, the deposition and coating conditions may be similar to those for formation of the HIL, although the deposition and coating conditions may vary according to a compound that is used to form the ETL. The ETL may be formed of the condensed-cyclic compound of Formula 1. Alternatively, a material that is used to form the ETL may be a material that stably transports electrons injected from the electron injecting electrode (cathode) and any known material may be used. Examples of materials for forming the ETL include a quinoline derivative, tris(8-quinolinorate)aluminum ($Alq_3$), TAZ, Balq, and beryllium bis(benzoquinolin-10-olate) ($bebq_2$), but are not limited thereto.

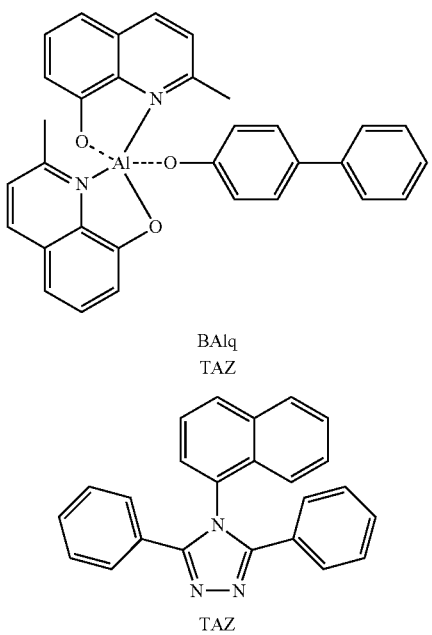

BAlq
TAZ

TAZ

The thickness of the ETL may be about 100 Å to about 1000 Å, and for example, about 150 Å to about 500 Å. When the thickness of the ETL is within this range, the ETL may have satisfactory electron transporting ability without a substantial increase in driving voltage.

Then, an EIL may be formed on the ETL. A material for forming the EIL is not limited as long as it allows electrons to be easily injected from the cathode.

Examples of materials for forming the EIL include LiF, NaCl, CsF, $Li_2O$, and BaO, which are known in the art. Deposition conditions for forming the EIL are similar to those for formation of the HIL, although the deposition conditions may vary according to a material that is used to form the EIL.

The thickness of the EIL may be about 1 Å to about 100 Å, specifically about 3 Å to about 90 Å. When the thickness of the EIL is within this range, the EIL may have satisfactory electron injection ability without a substantial increase in driving voltage.

Finally, the second electrode 17, which may be a transparent electrode, is disposed on the organic layer 15. The second electrode 17 may be a cathode that is an electron injection electrode. Here, a second electrode forming metal may be a metal having a low work function, an alloy having a low work function, an electro-conductive compound, or mixtures thereof. The second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In addition, the transmission electrode may be formed of ITO or IZO to manufacture a top-emission type light-emitting device.

Hereinafter, one or more embodiments of the present embodiments will be described in detail with reference to the following examples. However, these examples are not intended to limit the purpose and scope of the one or more embodiments.

EXAMPLES

Synthesis Example 1

Synthesis of Compounds F and G

Compounds F and G were synthesized through Reaction Scheme 2 below:

Reaction Scheme 2

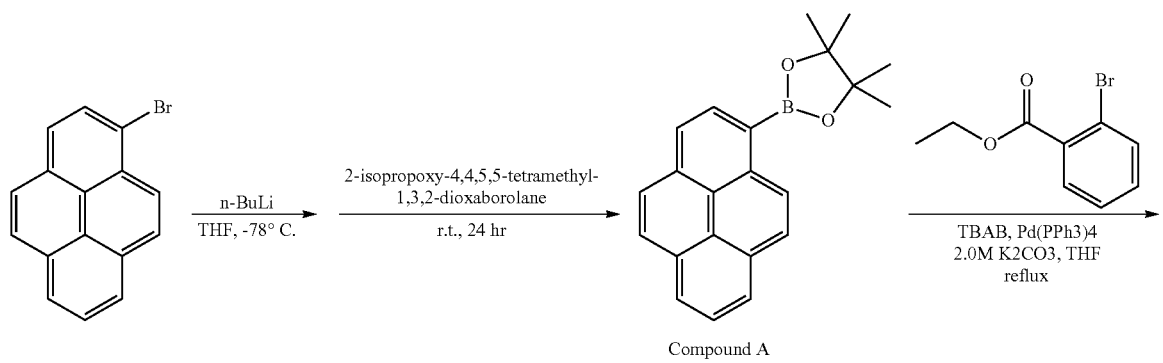

Compound A

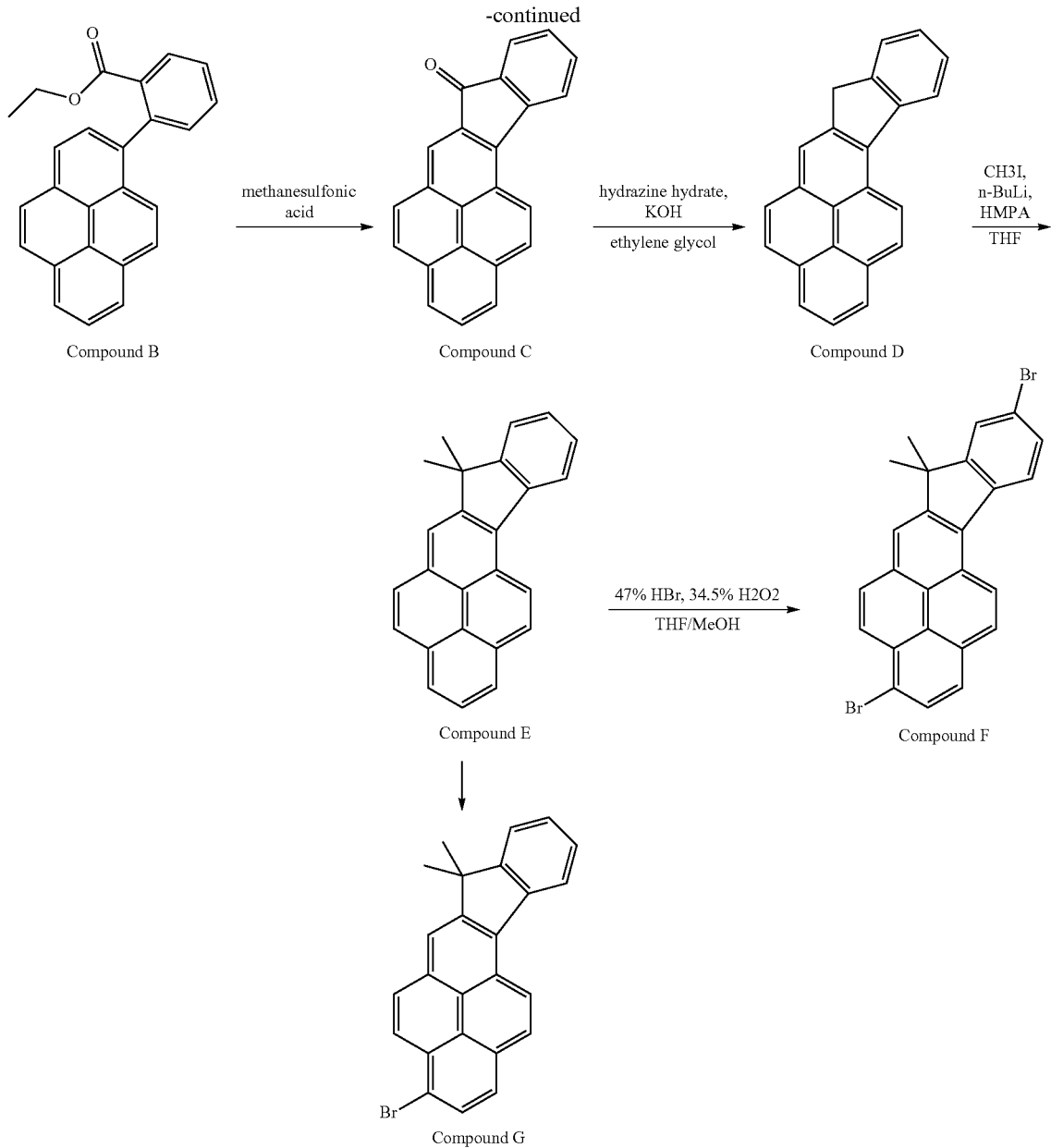

Synthesis of Compound A 100 g (355.68 mmol) of 2-bromopyrene was mixed with 1 L of tetrahydrofuran (THF) in a flask, the temperature of the mixture in the flask was decreased to −78° C., 213.4 ml (533.52 mmol) of 2.5M n-butyllithium (n-BuLi) in hexanes was slowly added dropwise to the dilution under a nitrogen atmosphere and then the resulting mixture thereof was stirred for 30 minutes. 99.41 mL (487.28 mmol) of 2-isopropoxy-4,4,5,5-tetramethyl-1,3,2-dioxaborolane was slowly to the reaction mixture, and then the flask was allowed to warm to room temperature.

The reaction was stopped by the addition of 1N (hydrochloric acid) HCl, and then were extracted with ethyl acetate (EA). Then, the extract was washed with water and brine, dried over magnesium sulfate (MgSO$_4$), and concentrated under reduced pressure. The concentrate was suspended in hexane and collected to give 75 g (yield=64%) of solid Compound A.

$^1$H-NMR (CDCl$_3$, 300 MHz) δ 1.48 (s, 12H), 7.97-8.04 (m, 3H), 8.07-8.22 (m, 4H), 8.53 (d, J=6.9 Hz, 1H), 8.06 (d, J=9.3 Hz, 1H).

Synthesis of Compound B 85 g (258.98 mmol) of 4,4,5,5-tetramethyl-2-(pyren-1-yl)-1,3,2-dioxaborolane, 45.23 mL (284.88 mmol) of ethyl 2-bromobenzoate, 83.49 g (258.98 mmol) of tetrabutylammonium bromide, 259 mL (517.96 mmol) of 2M potassium carbonate, and 14.96 g (12.95 mmol) of Pd(PPh$_3$)$_4$ were combined in toluene. The resultant mixture was stirred while increasing the temperature to ?, for 12 hours. The reaction was stopped by adding water to the mixture, and was extracted with ethyl acetate. The organic extract was washed with water and brine, dried over MgSO$_4$, and then concentrated under reduced pressure. The concentrate was subjected to column chromatography (ethyl acetate:Hexane (HEX)=1:50) so as to give 83 g (yield=91.5%) of thin light yellow solid Compound B.

$^1$H-NMR (CDCl$_3$, 300 MHz) δ 0.38 (t, J=6.9 Hz, 3H), 3.66-3.81 (in, 2H), 7.50 (d, J=6.9 Hz, 1H), 7.56-7.61, (m, 1H), 7.65-7.70 (m, 1H), 7.75 (d, J=9.3 Hz, 1H), 7.87 (d, J=7.8 Hz, 1H), 7.96-8.03 (m, 2H), 8.11 (m, 2H), 8.13-8.14 (m, 2H), 8.20-8.22 (m, 2H).

Synthesis of Compound C 35 g (99.88 mmol) of Compound B was added to 500 mL of methanesulfonic acid, and the resultant reaction mixture was stirred at 75° C. for about 4 hours. After checking that a starting material has disappeared by a thin layer chromatography (TLC), the reaction mixture was cooled down to 0° C. A red solid formed on cooling. The reaction mixture was stirred and the precipitate was collected by filtration. The filtrate was over with MgSO$_4$ and concentrated under reduced pressure to give 29 g (yield=95%) of red solid Compound C.

$^1$H-NMR (300 MHz) δ 7.97-7.99 (m, 4H), 8.05-8.15 (m, 4H), 8.32 (m, 1H), 8.44-8.49 (m, 2H) 8.75 (d, J=7.8 Hz, 1H), 9.36 (s, 1H).

Synthesis of Compound D 30 g (98.57 mmol) of Compound C was added to 500 mL of ethylene glycol, and followed by the addition of 148.08 mL (2957.1 mmol) of hydrazine hydrate. 132.74 g (2365.8 mmol) of potassium hydroxide was next added to the reaction mixture, and the reaction mixture was stirred overnight at a temperature from 180° C. to 190° C. Next, the reaction mixture was cooled down to room temperature, and then poured into ice water. A precipitate was formed on neutralizing the reaction mixture by the slow addition of 2N HCl. The precipitate was collected by filtration and was dissolved in methylene chloride (MC) to give an organic layer. The organic layer was dried over MgSO$_4$, and then concentrated under reduced pressure. Accordingly, 10 g (yield=35%) of yellow solid Compound D was obtained.

$^1$H-NMR (CDCl$_3$, 300 MHz) δ 4.29 (s, 2H), 7.41 (t, J=7.5 Hz, 1H), 7.55 (t, J=7.5 Hz, 1H), 7.72 (d, J=7.5 Hz, 1H), 8.00-8.09 (m, 3H), 8.20-8.27 (m, 3H), 8.35 (s, 1H), 8.59 (d, J=7.5 Hz, 1H), 9.02 (d, J=6.3 Hz, 1H).

Synthesis of Compound E 55.1 mL (137.76 mmol) of 2.5M n-BuLi in hexanes was put into a flask at −78° C., and then 16 g (55.1 mmol) of Compound D that has been dissolved in dried THF, was slowly added to the flask at −78° C. To the resultant reaction mixture was added 8.58 mL (137.76 mmol) of methyl iodide at −78° C., and the temperature was slowly increased to room temperature, and the reaction mixture was stirred for about 2 to 3 hours. Water was poured to the reaction mixture and then the reaction mixture was neutralized with 2N HCl. The reaction mixture were extracted with melthylene chloride, dried over MgSO$_4$, concentrated under reduced pressure, and then purified with column chromatography (ethyl acetate:hexane=1:100) to give obtain 11 g (yield=63%) of yellow solid Compound E.

$^1$H-NMR (CDCl$_3$, 300 MHz) δ 1.63 (s, 6H), 7.41 (t, J=7.2 Hz, 1H), 7.50 (t, J=7.2 Hz, 1H), 7.60 (d, J=7.5 Hz, 1H), 7.98 (t. J=7.2 Hz, 1H), 8.09-8.16 (m, 2H), 8.19-8.26 (m, 4H), 8.53 (d, J=7.5 Hz, 1H), 9.00 (d, J=9.3 Hz, 1H).

Synthesis of Compound F 11 g (34.55 mmol) of Compound E was dissolved in 80 mL of THF in a 1 L round-bottom flask (RBF), and then 400 mL of methanol (MeOH) was slowly added to the RBF. 9.5 mL (76.00 mmol) of 48% hydrobromic acid was slowly added to the reactant in the resultant reaction mixture at 0° C., followed by the slow addiction of 34.5% The temperature of the resultant reaction mixture was slowly increased from 0° C. to room temperature, while stirring the reaction mixture. After 2 the precipitate formed was filtered, dissolved in methylene chloride, washed with water, neutralized saturated NaHCO$_3$ solution, dried over MgSO$_4$, and then concentrated under reduced pressure. The concentrate was purified with column chromatography to give 5.2 g (yield=31.6%) of yellow solid Compound F.

$^1$H-NMR (CDCl$_3$, 300 MHz) δ 1.70 (s, 6H), 7.45 (t, J=7.2 Hz, 1H) 7.52 (t, J=7.8 Hz, 1H), 7.63 (d, J=7.2 Hz, 1H), 8.21 (d, J=9.3 Hz, 1H), 8.32 (s, 1H), 8.38 (d, J=9.3 Hz, 1H), 8.51-8.56 (m, 3H), 9.11 (d, J=9.9 Hz, 1H).

Synthesis of Compound G 7.8 g (yield=56%) of Compound G was obtained in the same manner as in Synthesis of Compound F, except that the reaction time was reduced to 8 hours, instead of 2 days.

$^1$H-NMR (CDCl$_3$, 300 MHz) δ 1.70 (s, 6H), 7.24 (t, J=7.1 Hz, 1H) 7.45 (t, J=7.8 Hz, 1H), 7.52 (t, J=7.8 Hz, 1H), 7.61 (d, J=7.1 Hz, 1H), 8.21 (d, J=9.3 Hz, 1H), 8.32 (s, 1H), 8.38 (d, J=9.3 Hz, 1H), 8.51-8.56 (m, 3H), 9.11 (d, J=9.9 Hz, 1H).

Synthesis Example 2

Synthesis of Compound 3

Compound 3 was synthesized through Reaction Scheme 3 below:

Reaction Scheme 3

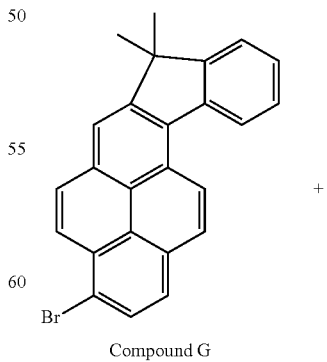

Compound G

Reaction Scheme 4

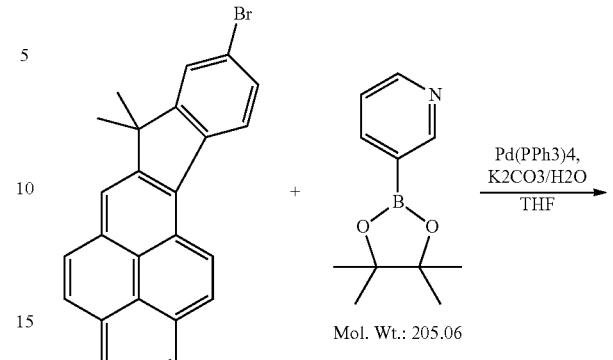

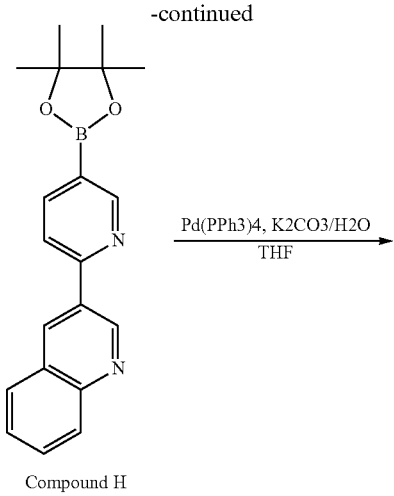

Compound H

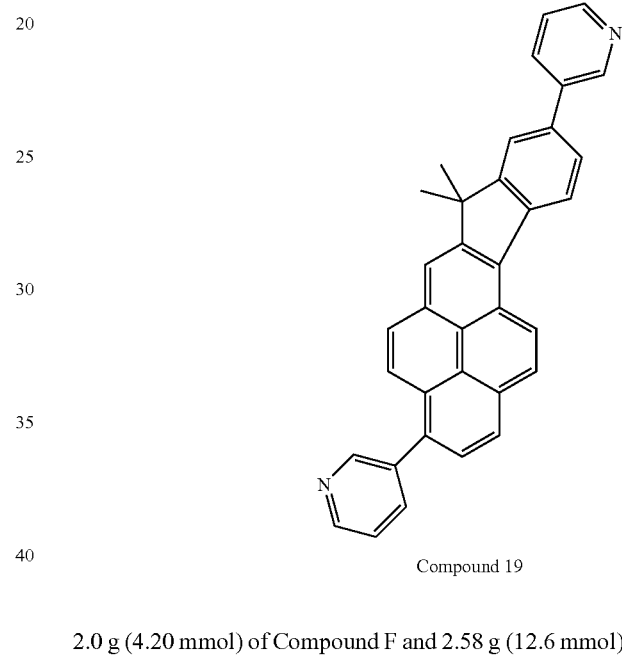

Compound 3

Compound 19

2.0 g (5.0 mmol) of Compound G and 1.84 g (5.5 mmol) of Compound H were added to a THF solution of 2.07 g (15.0 mmol) potassium carbonate, 173 mg (3 mol %) of Pd(PPh$_3$)$_4$ was added to the resultant reaction mixture with stirring, and the reaction mixture was heated for 24 hours. The mixture was cooled to room temperature extracted with dichloromethane. The organic layer was collected, dried over anhydrous magnesium sulfate and concentrated under reduced pressure. The concentrate was subjected to a column chromatography (ethyl acetate:dichloromethane=3:7) to give 2.07 g (yield=79%) of yellow solid Compound 3. The structure of Compound 3 was identified using $^1$H-NMR).

H NMR (CDCl$_3$, 300 MHz) δ 9.21 (1H), 8.82 (1H), 8.73 (1H), 8.18-8.03 (4H), 7.81 (1H), 7.71-7.60 (8H), 7.45-7.43 (2H), 7.24 (2H), 1.71 (6H)

Synthesis Example 3

Synthesis of Compound 19

Compound 19 was synthesized through Reaction Scheme 4 below:

2.0 g (4.20 mmol) of Compound F and 2.58 g (12.6 mmol) of 3-pyridylboron acid pinacol ester were added to THF solution of 2.32 g (16.8 mmol) potassium carbonate, to this reaction mixture was added, 194 mg (4 mol %) of Pd(PPh$_3$)$_4$ was added with stirring, and the resultant reaction mixture was heated for 24 hours. The reaction mixture was cooled to room temperature and extracted with dichloromethane. Then, the organic layer was collected, dried over anhydrous magnesium sulfate and concentrated under reduced pressure. The concentrate was dried over column chromatography (ethyl acetate: dichloromethane=3:7) to give 1.59 g (yield=80%) of yellow solid Compound 19. The structure of Compound 19 was identified using $^1$H-NMR.

H NMR (CDCl3, 300 MHz) δ 8.72 (2H), 8.51 (2H), 8.18-8.12 (2H), 8.02-7.97 (3H), 7.85-7.81 (2H), 7.71-7.65 (5H), 7.45-7.41 (2H), 1.72 (6H)

Synthesis Example 4

Synthesis of Compound 40

Compound 40 was synthesized through Reaction Scheme 5 below:

Reaction Scheme 5

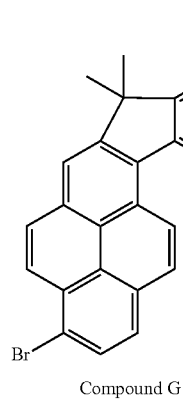

Compound G

Compound 40

Compound 40 was synthesized in the same manner as Synthesis Example 3, except that Compound G was used instead of Compound F, and phenylboron acid was used instead of 3-pyridylboron acid pinacol ester (yield=84%). The structure of Compound 40 was identified using $^1$H-NMR.

H NMR (CDCl$_3$, 300 MHz) δ 8.21 (1H), 8.06-8.01 (2H), 7.81 (1H), 7.78-7.62 (5H) 7.48-7.43 (3H), 7.32-7.25 (4H), 1.70 (6H)

Synthesis Example 5

Synthesis of Compound 35

Compound 35 was synthesized through Reaction Scheme 6 below:

Reaction Scheme 6

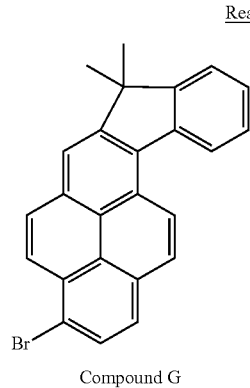

Compound G

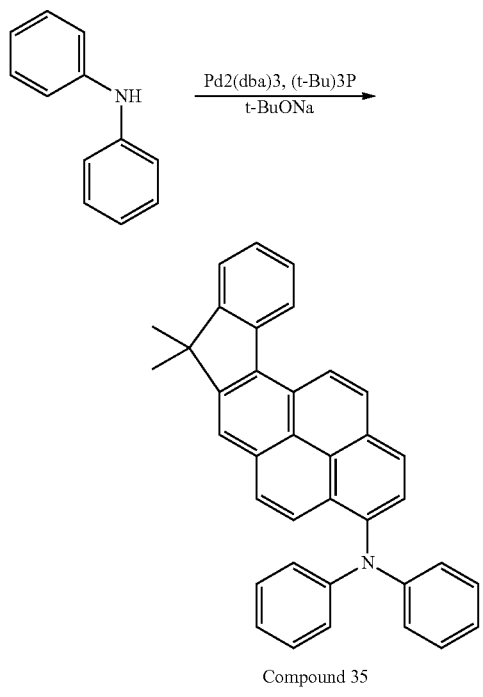

Compound 35

2 g (5.0 mmol) of Compound G and 1.28 g (7.55 mmol) of diphenylamine was dissolved in 50 mL of toluene. To this reaction mixture was added 2.40 g (25 mmol) of t-BuONa, 90.6 mg (2 mol %) of tris(dibenzylideneacetone)bispalladium (0) (Pd$_2$(dba)$_3$), and 20 mg (2 mol %) of (t-Bu)$_3$P were added thereto, and then the resultant reaction mixture was stirred for 4 hours at 90° C.

The reaction mixture was extracted 3 times by with 50 mL of dichloromethane and the organic layers were combined. The combined organic layers were dried over magnesium sulfate then evaporated to dryness. The residue was separately purified using silica gel column chromatography to give 1.76 g (yield=72%) of Compound 35. The structure of Compound 35 was identified using $^1$H-NMR.

$^1$H-NMR (300 MHz) δ 7.98 (1H) 7.87-7.81 (2H) 7.72-7.63 (5H), 7.44 (1H), 7.21 (1H), 7.05-6.97 (6H), 6.65-6.46 (5H), 1.71 (6H)

Synthesis Example 6

Synthesis of Compound 34

Compound 34 was synthesized through Reaction Scheme 7 below:

51

Reaction Scheme 7

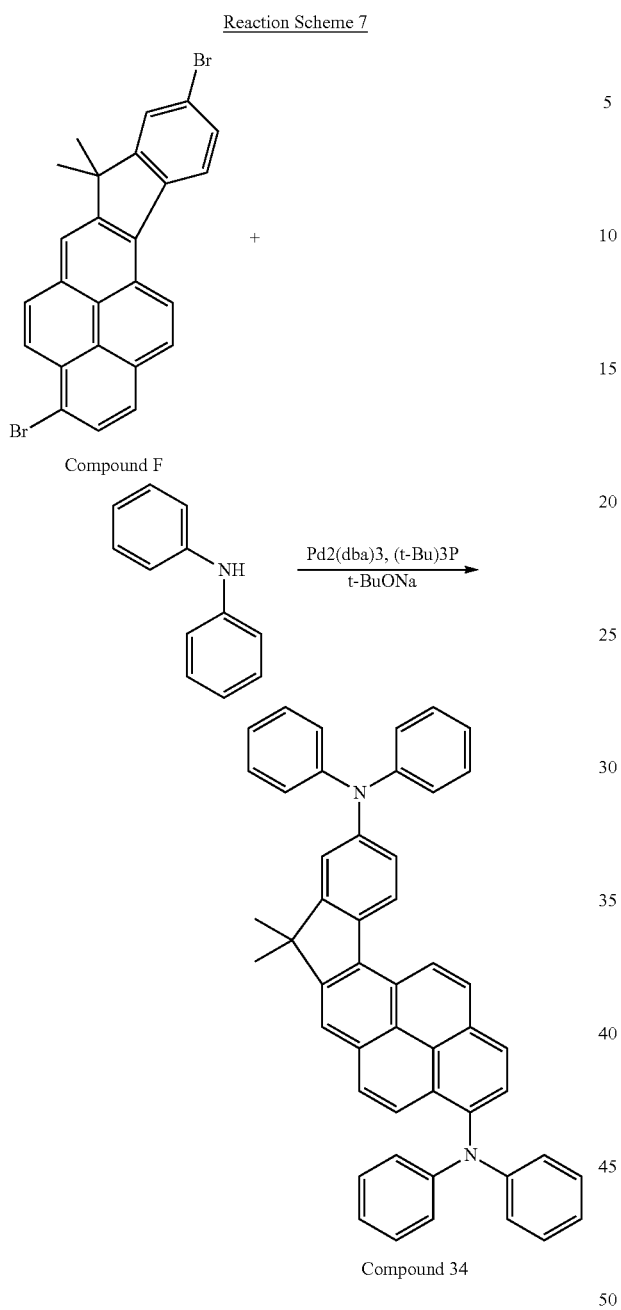

Compound 34

2.4 g (5.0 mmol) of Compound F and 2.54 g (15.0 mmol) of diphenylamine was dissolved in 100 mL of toluene. To this reaction mixture was added 2.40 g (25 mmol) of t-BuONa, 137 mg (3 mol %) of $Pd_2(dba)_3$, and 30 mg (3 mol %) of (t-Bu)3P and the resultant mixture was stirred for 6 hours at 90° C.

The reaction mixture was extracted 3 times with 100 mL of dichloromethane and the organic layers were combined. The combined organic layers were dried with magnesium sulfate then evaporated to dryness. The residue was subjected to silica gel column chromatography to give 2.27 g (yield=69%) of Compound 34. The structure of Compound 34 was identified using 1H-NMR.

$^1$H-NMR (300 MHz) δ 7.89 (1H), 7.82-7.80 (2H), 7.83-7.70 (4H), 7.11-7.04 (10H), 6.82 (2H), 6.65-6.59 (4H), 6.52-6.47 (7H), 1.72 (6H)

52

Synthesis Example 7

Synthesis of Compound 43

Compound 43 was synthesized through Reaction Scheme 8 below:

Reaction Scheme 8

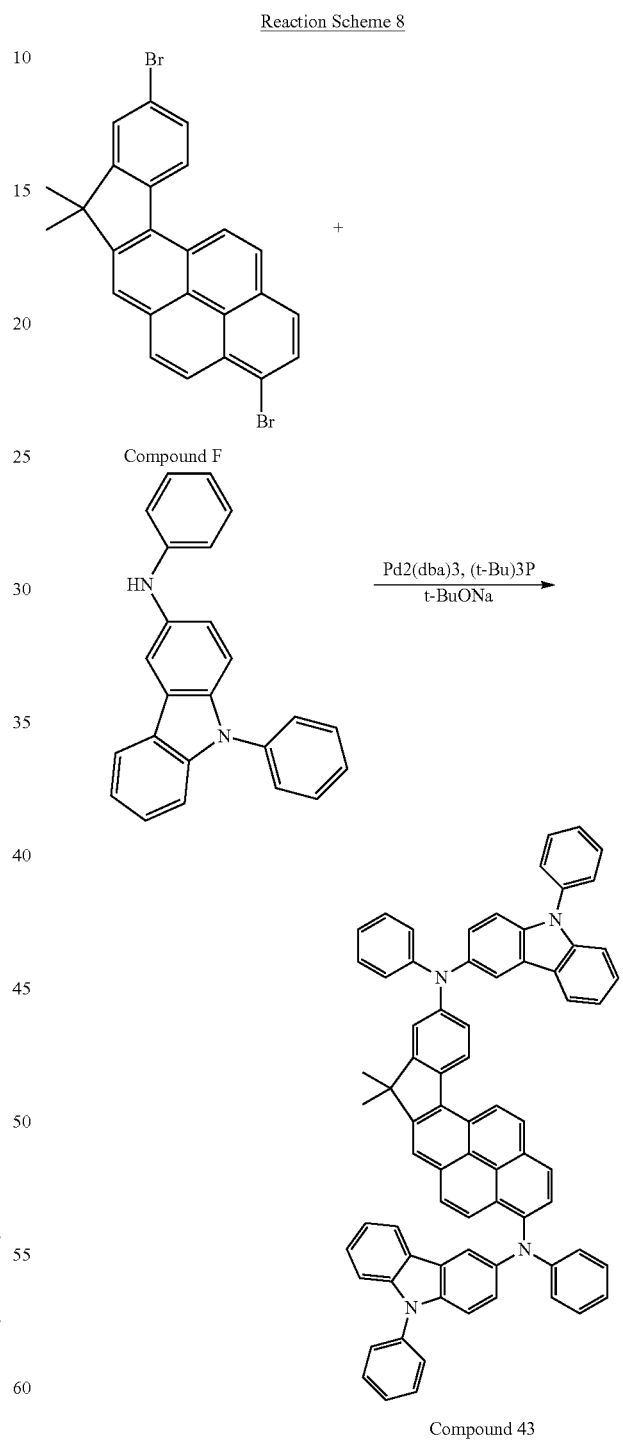

Compound 43

2.4 g (5.0 mmol) of Compound F and 5.01 g (15.0 mmol) of phenyl-(phenylcarbazole) was dissolved in 200 mL of toluene. To the resultant reaction mixture was added 2.40 g (25 mmol) of t-BuONa, 137 mg (3 mol %) of $Pd_2(dba)_3$, and 30 mg (3 mol %) of (t-Bu)$_3$P, and then the resultant reaction mixture was stirred for 6 hours at 90° C.

The reaction mixture was then extracted 3 times with 100 mL of dichloromethane and the organic layers were combined, dried over magnesium sulfate to evaporate the solvent. The residue was subjected to silica gel column chromatography to obtain 2.73 g (yield=56%) of Compound 43. The structure of Compound 43 was identified using $^1$H-NMR.

$^1$H-NMR (300 MHz) δ 7.87 (1H), 7.82 (1H), 7.76-7.72 (5H), 7.56 (2H), 7.42 (2H), 7.39-7.13 (12H), 7.08-6.98 (10H), 6.81-6.46 (9H), 6.28 (2H), 1.71 (6H)

Comparative Example 1

A 15 Ω/cm$^2$ (1200 Å) ITO glass substrate (available from Corning Co.) was cut to a size of 50 mm×50 mm×0.7 mm, ultrasonically washed with isopropyl alcohol for 5 minutes and then with pure water for 5 minutes, and washed again with UV ozone for 30 minutes. Then, m-MTDATA was vacuum deposited on the substrate to form a hole injection layer having a thickness of 750 Å, and then α-NPD was vacuum deposited on the hole injection layer to form a hole transport layer having a thickness of 150 Å. 97 wt % of DSA as a host and 3 wt % of TBPe as a dopant were deposited on the HTL to form an EML with a thickness of 300 Å. Alq3 was vacuum-deposited on the EML to form an ETL having a thickness of 200 Å. LiF was vacuum-deposited on the ETL to form an EIL having a thickness of 80 Å and Al was vacuum-deposited on the EIL to form a cathode having a thickness of 3000 Å.

Example 1

An OLED was manufactured in the same manner as in Comparative Example 1, except that Compound 34 was used instead of m-MTDATA to form the HTL.

Example 2

An OLED was manufactured in the same manner as in Comparative Example 1, except that Compound 40 was used instead of DSA as the host of the EML.

Example 3

An OLED was manufactured in the same manner as in Comparative Example 1, except that Compound 35 was used instead of TBPe as the dopant of the EML.

Example 4

An OLED was manufactured in the same manner as in Comparative Example 1, except that Compound 43 was used instead of Alq$_3$ to form the ETL.

Example 5

An OLED was manufactured in the same manner as in Comparative Example 1, except that Compound 19 was used instead of Alq$_3$ to form the ETL.

Example 6

An OLED was manufactured in the same manner as in Comparative Example 1, except that Compound 3 was used instead of Alq$_3$ to form the ETL.

Evaluation Example

Efficiency and half lifetime characteristics of the OLEDs manufactured in Comparative Example 1 and Examples 1 through 6 were measured using a PR650 (Spectroscan) Source Measurement Unit. (available from PhotoResearch, Inc.). The results are shown in Table 1 below.

TABLE 1

| | Compound | Use of Compound | Luminance Efficiency (cd/A) | Half Lifetime (hour) @ 1000 nit |
| --- | --- | --- | --- | --- |
| Example 1 | Compound 34 | Hole Transport Layer | 4.2 | 3700 |
| Example 2 | Compound 40 | Host | 4.3 | 4200 |
| Example 3 | Compound 35 | Dopant | 3.7 | 3800 |
| Example 4 | Compound 43 | Hole Transport Layer | 4.1 | 4200 |
| Example 5 | Compound 19 | Electron Transport Layer | 4.4 | 4500 |
| Example 6 | Compound 3 | Electron Transport Layer | 3.9 | 2600 |
| Comparative Example | — | — | 2.8 | 1400 |

Referring to Table 1, it can be confirmed that the OLEDs of Examples 1 through 6 have higher luminance efficiencies and half lifetime, compared to the OLED of Comparative Example 1.

An OLED including an organic layer containing the condensed-cyclic compound of Formula 1 above may have high efficiency and long durability.

While the present embodiments have been particularly shown and described with reference to exemplary embodiments thereof, it will be understood by those of ordinary skill in the art that various changes in form and details may be made therein without departing from the spirit and scope of the present embodiments as defined by the following claims.

What is claimed is:

1. A condensed-cyclic compound represented by Formula 1 below:

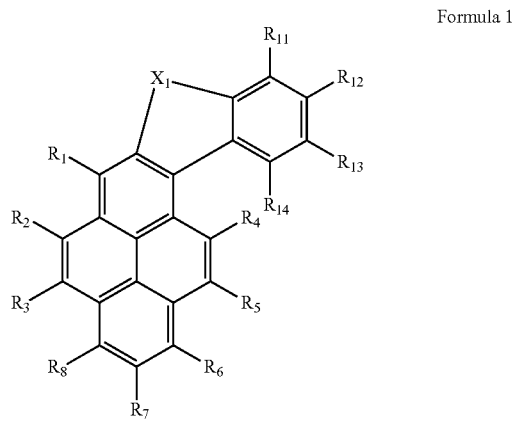

Formula 1 wherein R$_8$ and R$_7$ are not identical and are each independently selected from the group consisting of a hydrogen atom, a halogen atom, a hydroxyl group, a cyano group, a substituted or unsubstituted C$_1$-C$_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_1)_a$—$Ar_{11}$, and a group represented by —$N[$—$(Ar_2)_b$—$Ar_{12}][$—$(Ar_3)_c$—$Ar_{13}]$; or $R_8$ is connected to * of Formula 2 and $R_7$ is connected to *' of Formula 2 represented by:

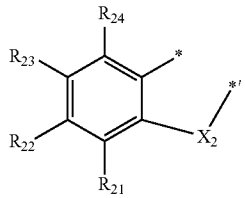

wherein $R_1$ through $R_6$, $R_{11}$ through $R_{14}$, and $R_{21}$ through $R_{24}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_4)_d$—$Ar_{14}$, and a group represented by —$N[$—$(Ar_5)_e$—$Ar_{15}][$—$(Ar_6)_f$—$Ar_{16}]$;

wherein $Ar_1$ through $Ar_6$ are each independently selected from the group consisting of a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and a substituted or unsubstituted $C_4$-$C_{30}$ heteroarylene group;

wherein $Ar_{11}$ through $Ar_{16}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group;

wherein a through f are each independently an integer from 0 to 10;

wherein the moieties represented by $Ar_1$ in the group represented by —$(Ar_1)_a$—$Ar_{11}$ are identical to or different from each other, the moieties represented by $Ar_e$ in the group represented by —$(Ar_2)_b$—$Ar_{12}$ are identical to or different from each other, the moieties represented by $Ar_3$ in the group represented by —$(Ar_3)_c$—$Ar_{13}$ are identical to or different from each other, the moieties represented by $Ar_4$ in the group represented by —$(Ar_4)_d$—$Ar_{14}$ are identical to or different from each other, the moieties represented by $Ar_5$ in the group represented by —$(Ar_5)_e$—$Ar_{15}$ are identical to or different from each other, and the moieties represented by $Ar_6$ in the group represented by $[$—$(Ar_6)_f$—$Ar_{16}]$ are identical to or different from each other;

wherein $X_1$ and $X_2$ are each independently a divalent linking group selected from the group consisting of —$C(Q_1)(Q_2)$- and —$N(Q_3)$-; and wherein $Q_1$ through $Q_3$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group.

2. The condensed-cyclic compound of claim 1, wherein $R_1$, $R_2$ $R_3$ $R_4$, $R_5$, $R_6$, and $R_7$ are hydrogen;

$R_8$ is selected from the group consisting of a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_1)_a$—$Ar_{11}$, and a group represented by —$N[$—$(Ar_2)_b$—$Ar_{12}][$—$(Ar_3)_c$—$Ar_{13}]$;

$R_{11}$, $R_{12}$, $R_{13}$ and $R_{14}$ are each independently selected from the group consisting of hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_4)_d$—$Ar_{14}$, and a group represented by —$N[$—$(Ar_5)_e$—$Ar_{15}][$—$(Ar_6)_f$—$Ar_{16}]$;

$Ar_1$, $Ar_2$, $Ar_3$, $Ar_4$, $Ar_5$ and $Ar_6$ are each independently selected from the group consisting of a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and a substituted or unsubstituted $C_4$-$C_{30}$ heteroarylene group; and $Ar_{11}$ and $Ar_{16}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group.

3. The condensed-cyclic compound of claim 2, wherein a, b, c, d, e and f are each independently 0, 1, or 2.

4. The condensed-cyclic compound of claim 2, wherein $Ar_1$, $Ar_2$, $Ar_3$, $Ar_4$, $Ar_5$ and $Ar_6$ are each independently selected from the group consisting of a pyridinylene group, a quinolinylene group, a benzimidazolylene group, an imidazopyridinylene group, an imidazopyrimidinylene group, a phenylene group, a $C_1$-$C_{10}$ alkyl phenylene group, a carbazolylene group, a phenylcarbazolylene group, a fluorenylene group, a $C_1$-$C_{10}$ alkylfluorenylene group, a di($C_1$-$C_{10}$alkyl)fluorenylene group, an ethylene group, and a naphthylene group.

5. The condensed-cyclic compound of claim 2, wherein $Ar_{11}$ $Ar_{12}$, $Ar_{13}$, $Ar_{14}$, $Ar_{15}$ and $Ar_{16}$ are each independently selected from the group consisting of a methyl group, ethyl, a propyl group, a butyl group, a methoxy group, an ethoxy group, a propoxy group, a butoxy group, a pyridinyl group, a quinolinyl group, a benzimidazolyl group, an imidazopyridinyl group, an imidazopyrimidinyl group, a phenyl group, a carbazolyl group, a fluorenyl group, a di($C_1$-$C_{10}$alkyl)fluorenyl group, a naphthyl group, and a functional group prepresented by the formula

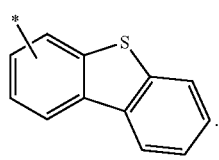
6. The condensed-cyclic compound of claim 2, wherein $R_8$ is selected from the group consisting of functional groups represented by Formulae 3A through 3O below
Formula 3A
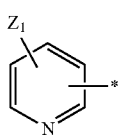
Formula 3B
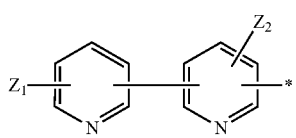
Formula 3C
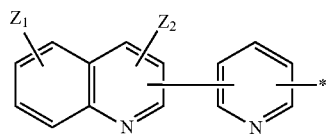
Formula 3D
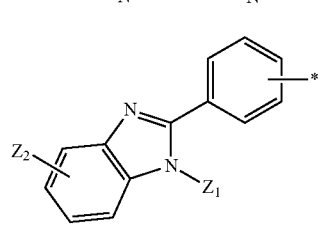
Formula 3E
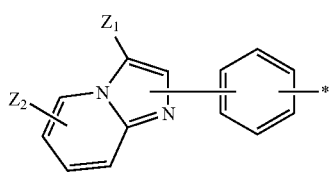
Formula 3F
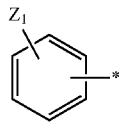
Formula 3G
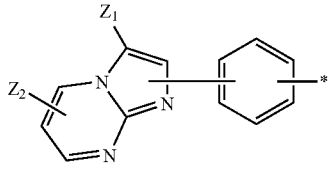
Formula 3H
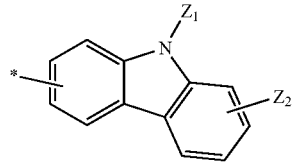
Formula 3I
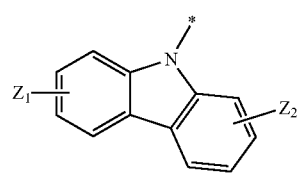
Formula 3J
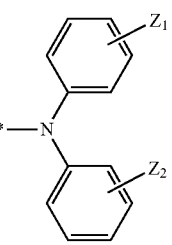
Formula 3K
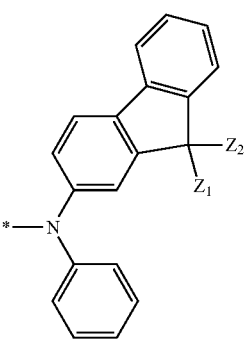
Formula 3L
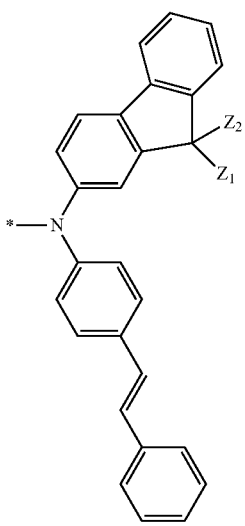
Formula 3M
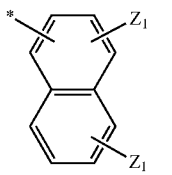

Formula 3N
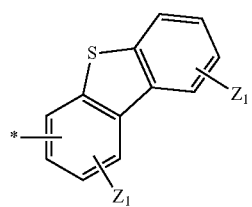
Formula 3O
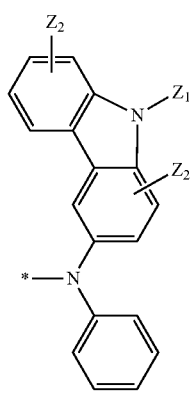
and $R_{11}$, $R_{12}$, $R_{13}$ and $R_{14}$ are each independently selected from the group consisting of hydrogen and functional groups represented by Formulae 3A through 3O below:
Formula 3A
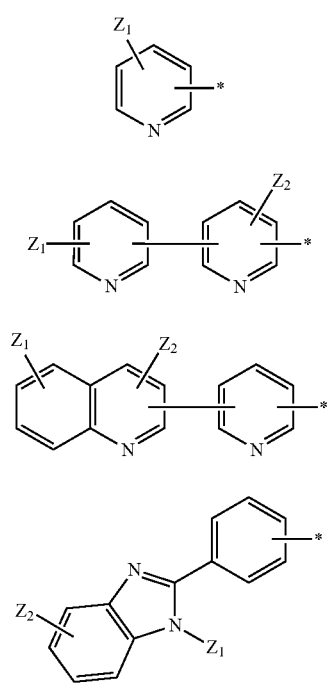
Formula 3B
Formula 3C
Formula 3D
Formula 3E
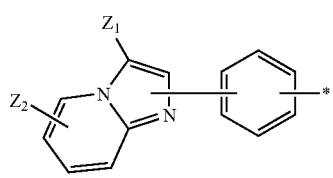
Formula 3F
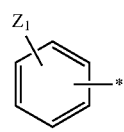
Formula 3G
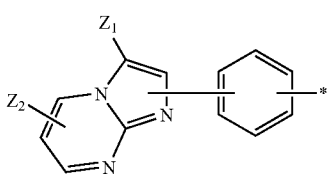
Formula 3H
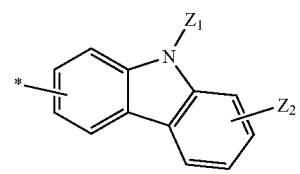
Formula 3I
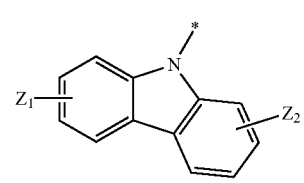
Formula 3J
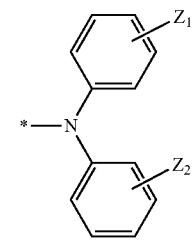
Formula 3K
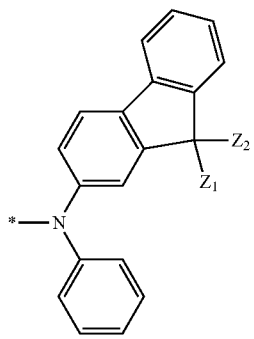

-continued

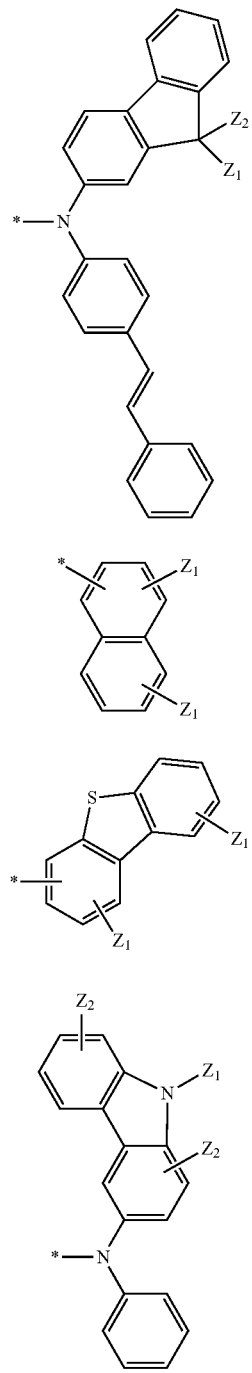

Formula 3L

Formula 3M

Formula 3N

Formula 3O wherein, in Formulae 3A through 3O, $Z_1$ and $Z_2$ are each independently selected from the group consisting of hydrogen, a methyl group, an ethyl group, a propyl group, a butyl group, a methoxy group, an ethoxy group, a propoxy group, a butoxy group, a phenyl group, and a naphthyl group.

7. The condensed-cyclic compound of claim 2, wherein R8 is selected from the group consisting of functional groups represented by Formula 4A through 4R below

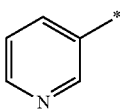

Formula 4A

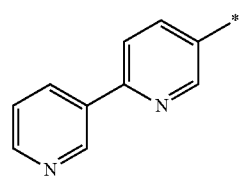

Formula 4B

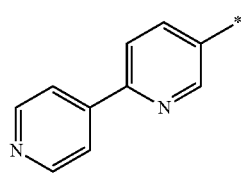

Formula 4C

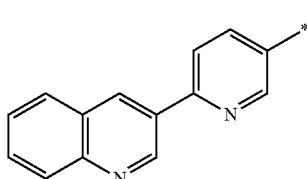

Formula 4D

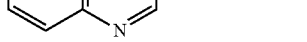

Formula 4E

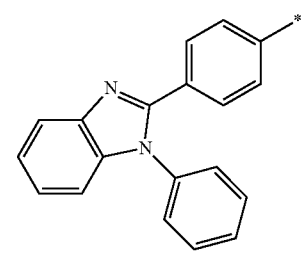

Formula 4F

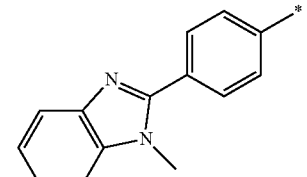

Formula 4G

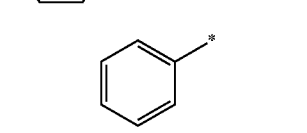

Formula 4H

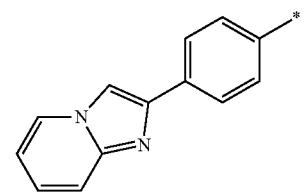

Formula 4I

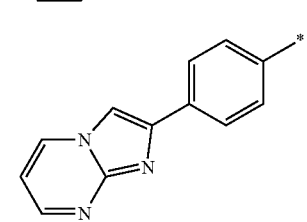

-continued
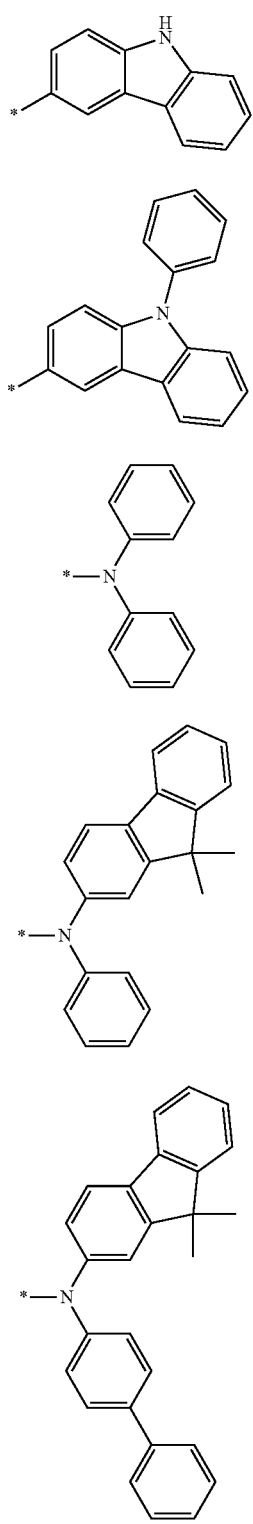
Formula 4J
Formula 4K
Formula 4L
Formula 4M
Formula 4N
-continued
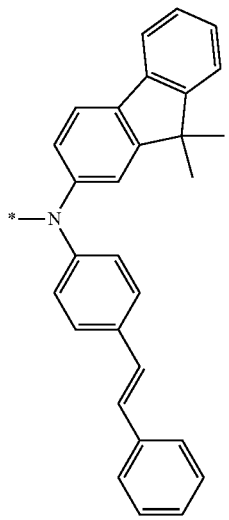
Formula 4O
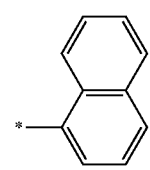
Formula 4P
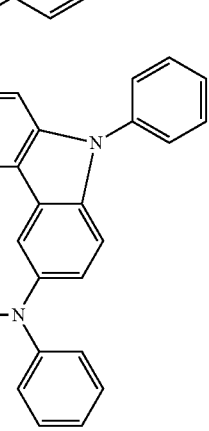
Formula 4Q
Formula 4R
and $R_{11}$ $R_{12}$, $R_{13}$ and $R_{14}$ are each independently selected from the group consisting of hydrogen and functional groups represented by Formulae 4A through 4R below:
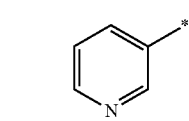
Formula 4A

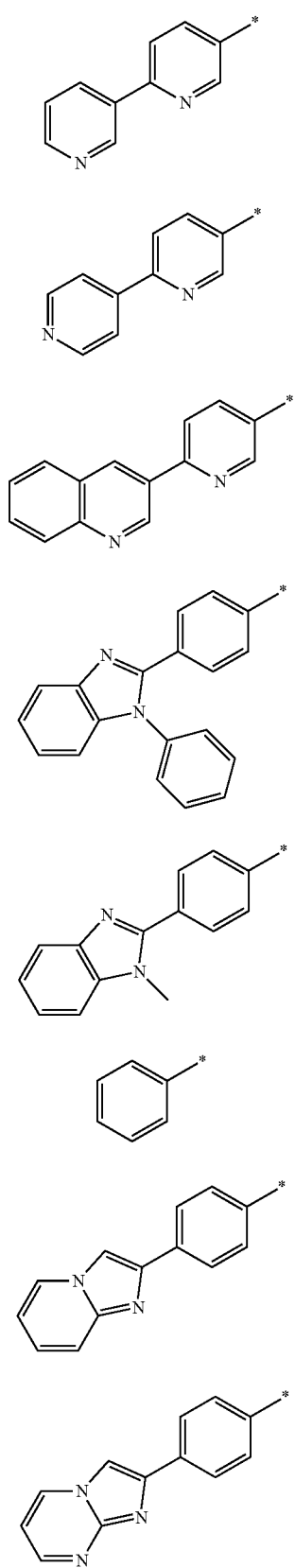
Formula 4B
Formula 4C
Formula 4D
Formula 4E
Formula 4F
Formula 4G
Formula 4H
Formula 4I
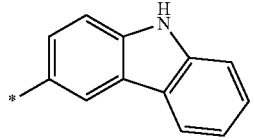
Formula 4J
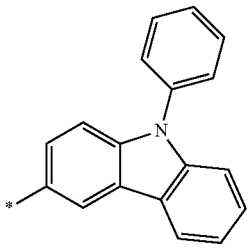
Formula 4K
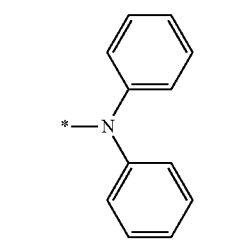
Formula 4L
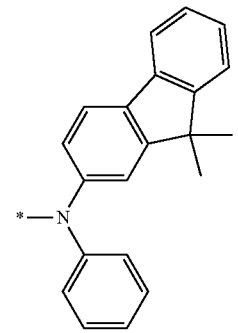
Formula 4M
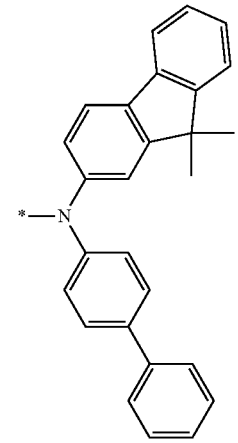
Formula 4N -continued Formula 4O

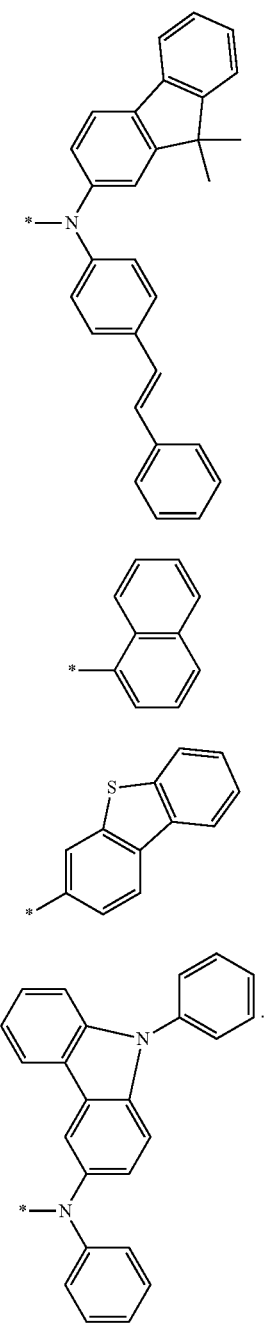

Formula 4P

Formula 4Q

Formula 4R

8. The condensed-cyclic compound of claim 2, wherein $Q_1$ through $Q_3$ are each independently selected from the group consisting of hydrogen, a $C_1$-$C_{30}$ alkyl group, a $C_1$-$C_{30}$ alkoxy group, a $C_5$-$C_{14}$ aryl group, and a $C_4$-$C_{14}$ heteroaryl group.

9. The condensed-cyclic compound of claim 1, wherein $R_8$ is connected to * of Formula 2 and $R_7$ is connected to *' of Formula 2 so as to be represented by Formula 1a below:

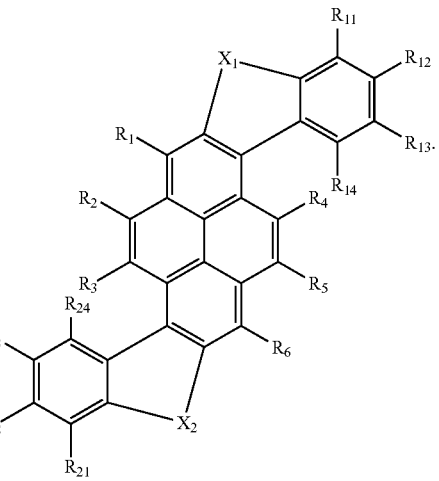

Formula 1a

10. The condensed-cyclic compound of claim 9, wherein $R_1$ $R_2$, $R_3$, $R_4$, $R_5$ and $R_6$ are hydrogen;

$R_{11}$ $R_{12}$, $R_{13}$, $R_{14}$ $R_{21}$ $R_{22}$, $R_{23}$ and $R_{24}$ are each independently selected from the group consisting of hydrogen, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a group represented by —$(Ar_4)_d$—$Ar_{14}$, and a group represented by —$N[—(Ar_5)_e—Ar_{15}][—(Ar_6)_f—Ar_{16}]$;

$Ar_4$, $Ar_5$ and $Ar_6$ are each independently selected from the group consisting of a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and a substituted or unsubstituted $C_4$-$C_{30}$ heteroarylene group; and $Ar_{14}$ and $Ar_{16}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group.

11. The condensed-cyclic compound of claim 9, wherein d, e and f are each independently 0, 1, or 2.

12. The condensed-cyclic compound of claim 9, $Ar_4$, $Ar_5$ and $Ar_6$ are each independently selected from the group consisting of a pyridinylene group, a quinolinylene group, a benzimidazolylene group, an imidazopyridinylene group, an imidazopyrimidinylene group, a phenylene group, a $C_1$-$C_{10}$ alkyl phenylene group, a carbazolylene group, a phenylcarbazolylene group, a fluorenylene group, a $C_1$-$C_{10}$ alkyl fluorenylene group, a di($C_1$-$C_{10}$ alkyl) fluorenylene group, an ethylene group, and a naphthylene group.

13. The condensed-cyclic compound of claim 9, wherein $Ar_{14}$, $Ar_{15}$ and $Ar_{16}$ are each independently selected from the group consisting of a methyl group, an ethyl group, a propyl group, a butyl group, a methoxy group, an ethoxy group, a propoxy group, a butoxy group, a pyridinyl group, a quinolinyl group, a benzimidazolyl group, an imidazopyridinyl group, an imidazopyrimidinyl group, a phenyl group, a carbazolyl group, a fluorenyl group, di(C₁-C₁₀ alkyl)fluorenyl group, a naphthyl group, and a functional group prepresented by the formula

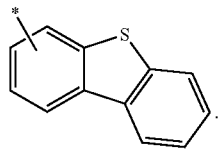

14. The condensed-cyclic compound of claim 9, wherein $R_{11}, R_{12}, R_{13}, R_{14}, R_{21}, R_{22}, R_{23}$ and $R_{24}$ are each independently selected from the group consisting of hydrogen and functional groups represented by Formulae 3A through 3O below:

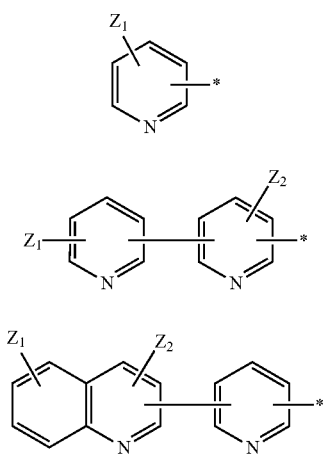

Formula 3A

Formula 3B

Formula 3C

Formula 3D

Formula 3E

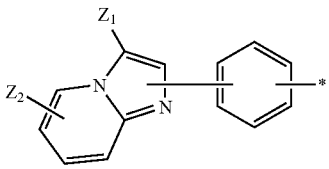

Formula 3F

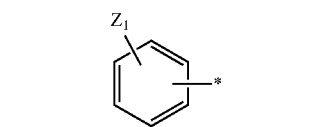

Formula 3G

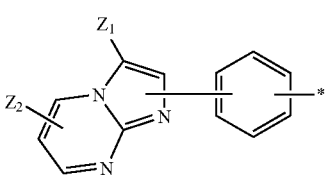

-continued

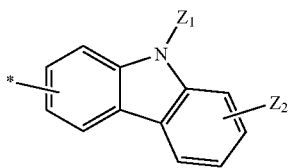

Formula 3H

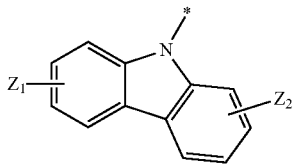

Formula 3I

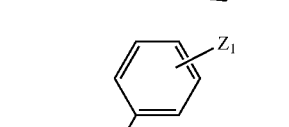

Formula 3J

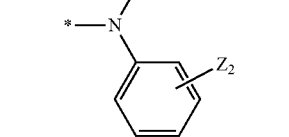

Formula 3K

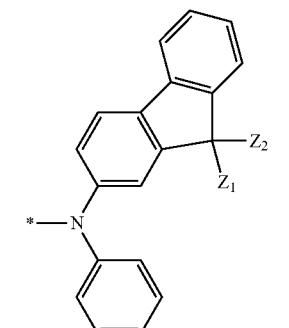

Formula 3L

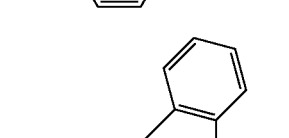

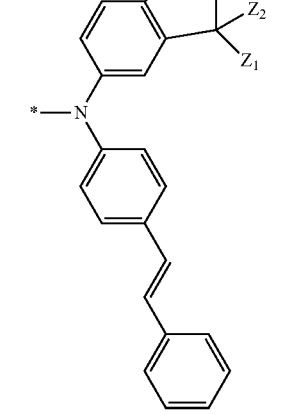

Formula 3M

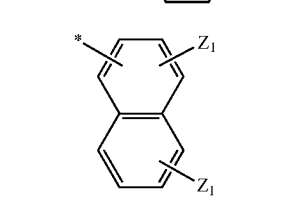

Formula 3N

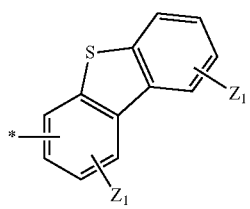

Formula 3O

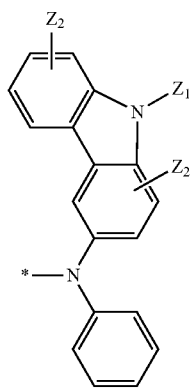

wherein, in Formulae 3A through 3O, $Z_1$ and $Z_2$ are each independently selected from the group consisting of hydrogen, a methyl group, an ethyl group, a propyl group, a butyl group, a methoxy group, an ethoxy group, a propoxy group, a butoxy group, a phenyl group, and a naphthyl group.

15. The condensed-cyclic compound of claim 9, wherein $R_{11}$ $R_{12}$, $R_{13}$ $R_{14}$ $R_{21}$ $R_{22}$, $R_{23}$ and $R_{24}$ are each independently selected from the group consisting of hydrogen and functional groups represented by Formulae 4A through 4R below:

Formula 4A

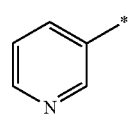

Formula 4B

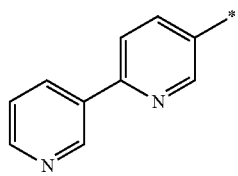

Formula 4C

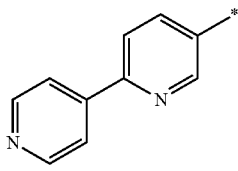

Formula 4D

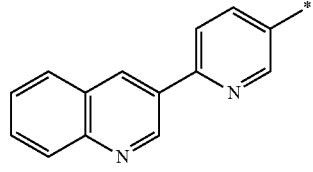

Formula 4E

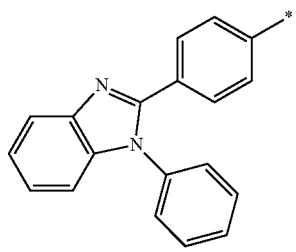

Formula 4F

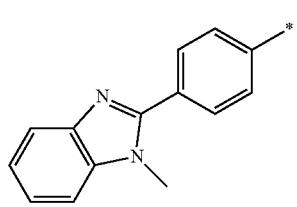

Formula 4G

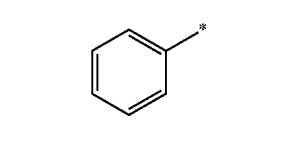

Formula 4H

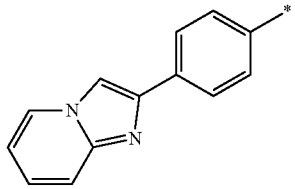

Formula 4I

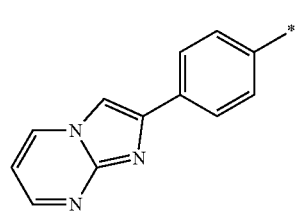

Formula 4J

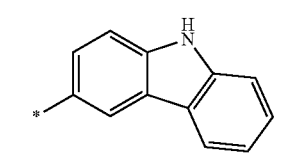

Formula 4K

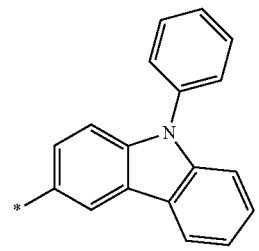

Formula 4L

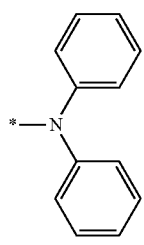

Formula 4M

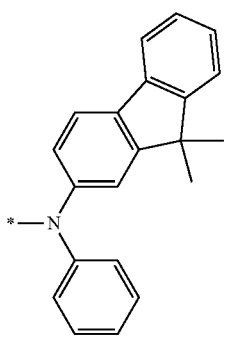

Formula 4N

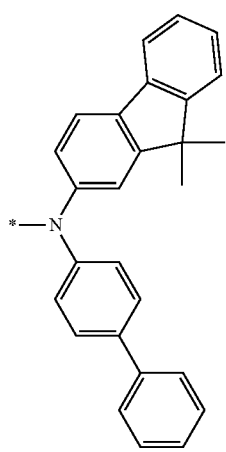

Formula 4O

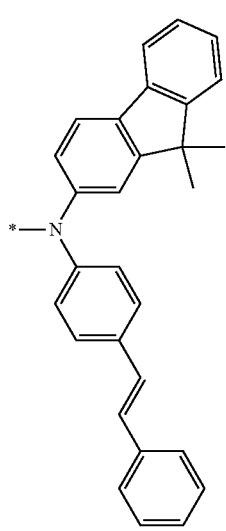

Formula 4P

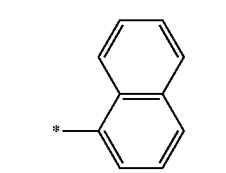

Formula 4Q

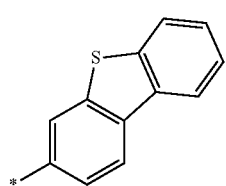

Formula 4R

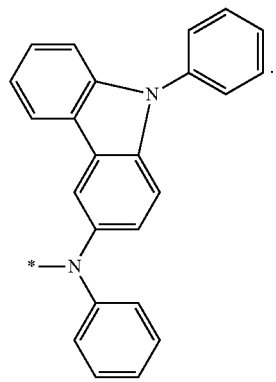

16. The condensed-cyclic compound of claim 9, wherein $Q_1$, $Q_2$ and $Q_3$ are each independently selected from the group consisting of hydrogen, a $C_1$-$C_{30}$ alkyl group, a $C_1$-$C_{30}$ alkoxy group, a $C_5$-$C_{14}$ aryl group, and a $C_4$-$C_{14}$ heteroaryl group.

17. A condensed-cyclic compound having the structure of compounds 1 to 6 and 13 to 43 below:

Compound 1

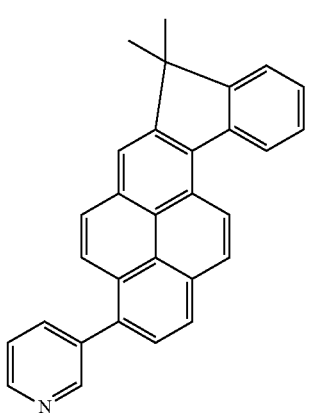

Compound 2

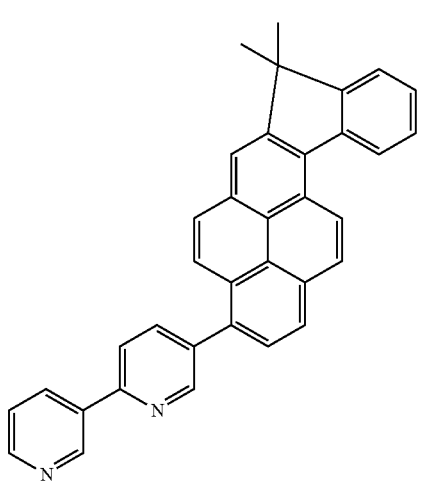

Compound 3
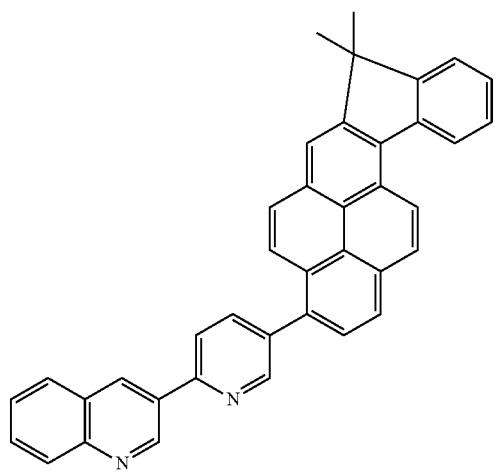
Compound 4
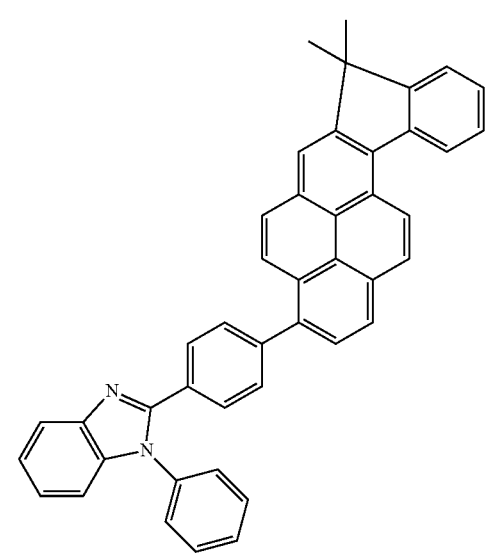
Compound 5
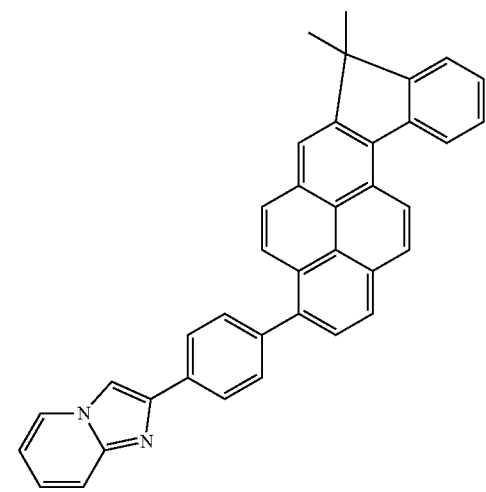
Compound 6
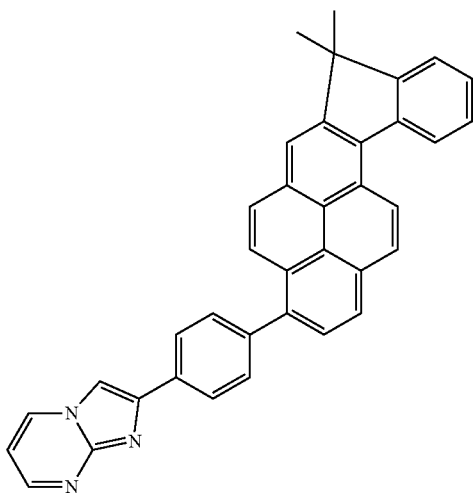
Compound 13
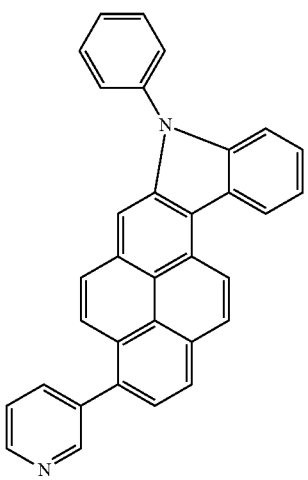
Compound 14
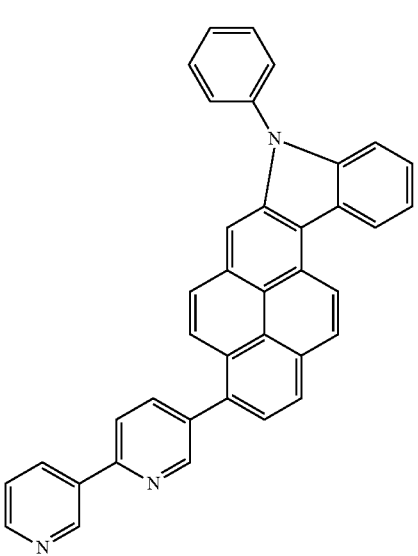

-continued
Compound 15
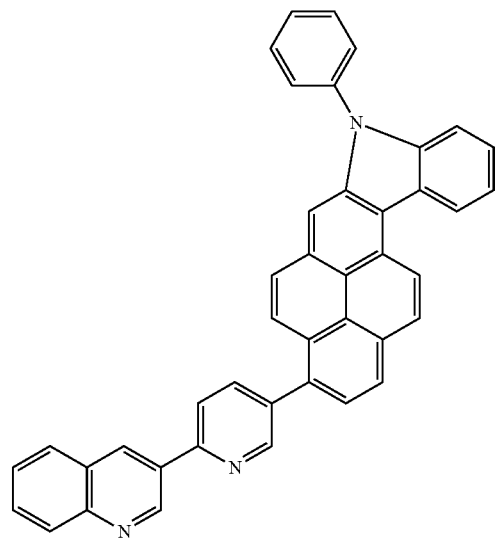
Compound 16
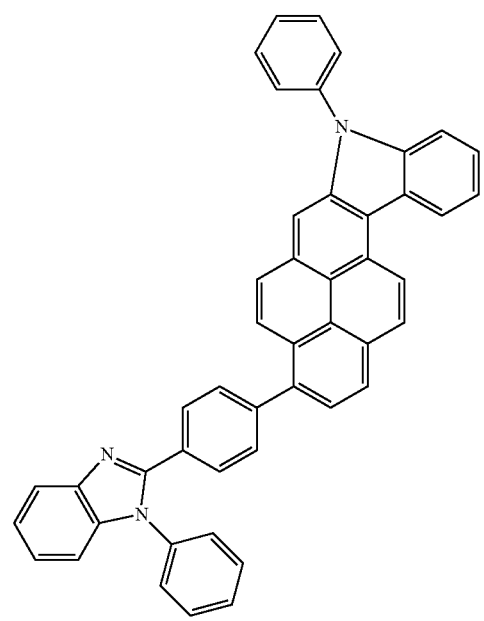
Compound 17
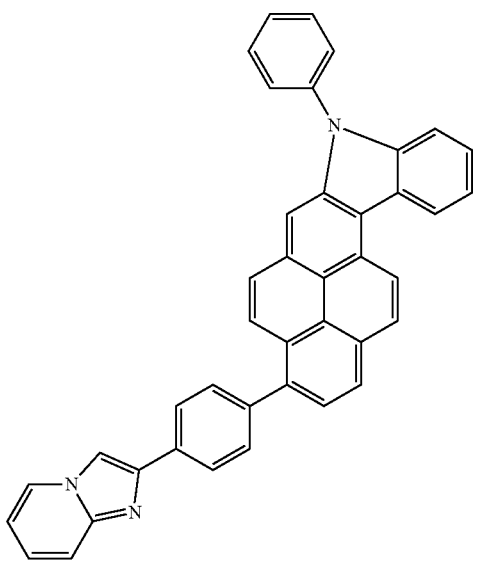
Compound 18
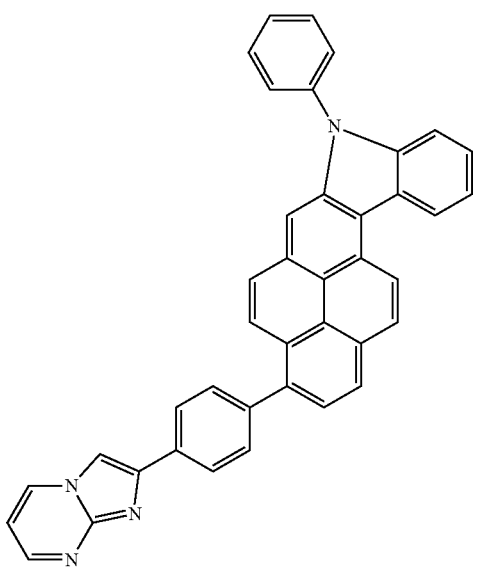
Compound 19
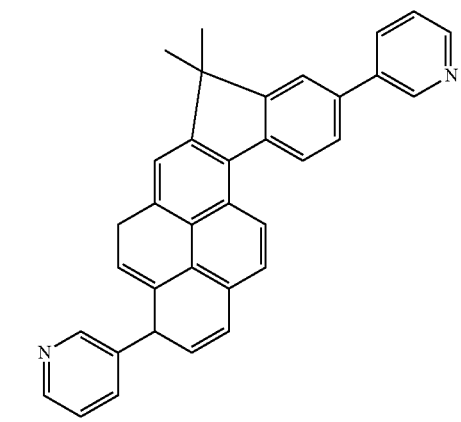

Compound 20
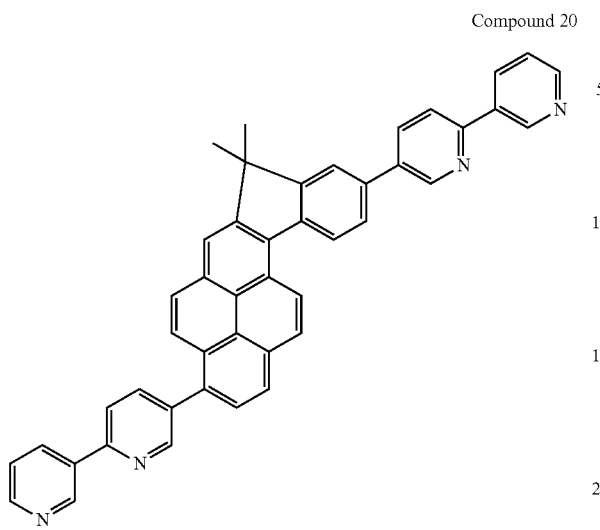
Compound 23
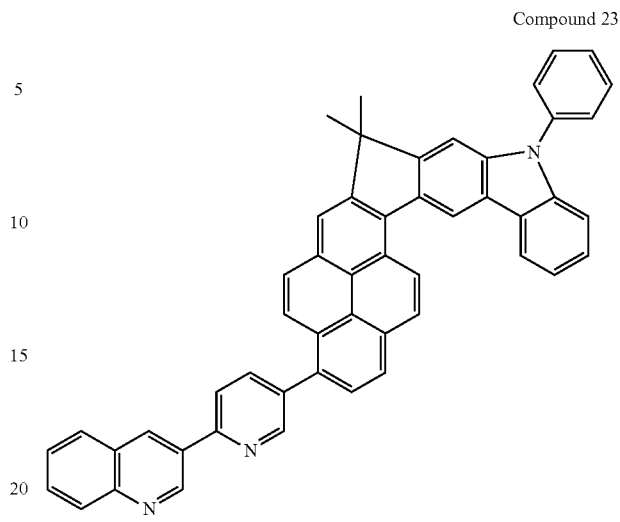
Compound 21
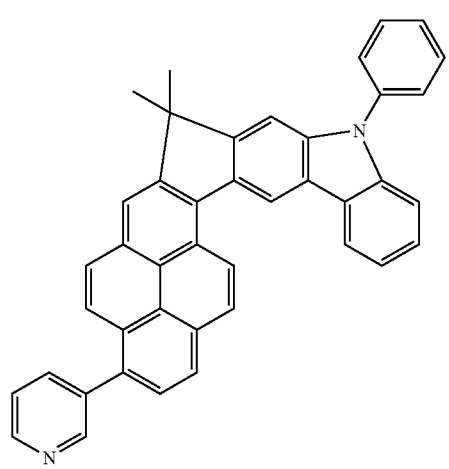
Compound 24
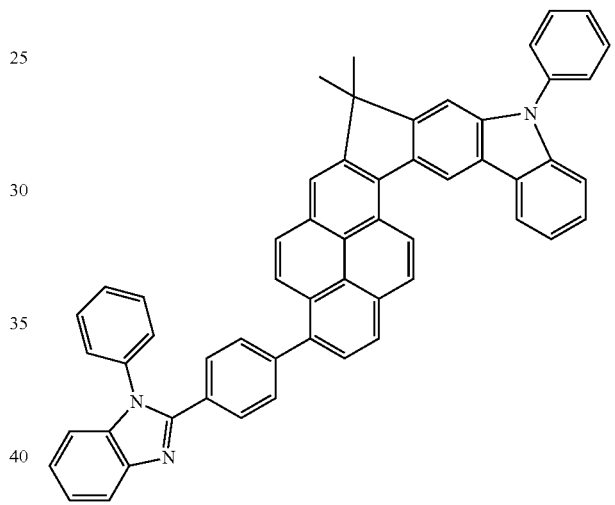
Compound 22
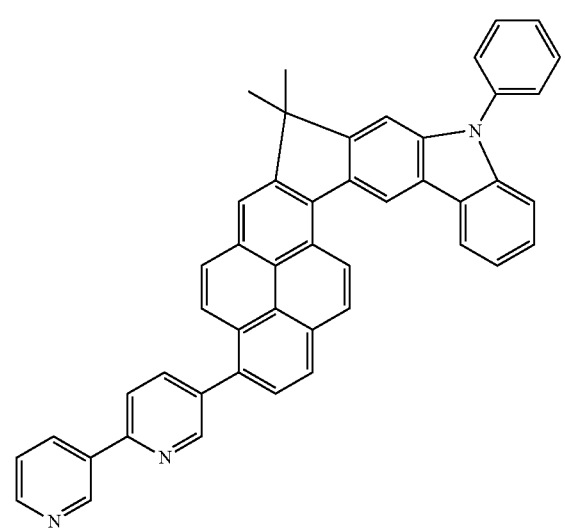
Compound 25
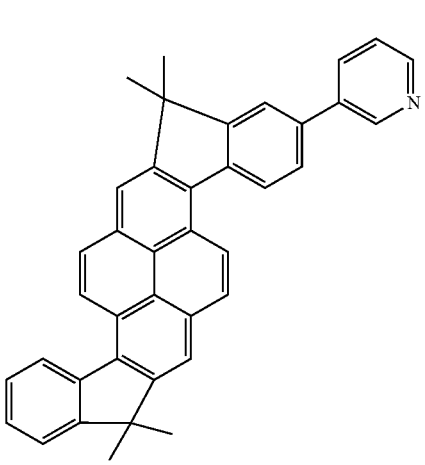

Compound 26
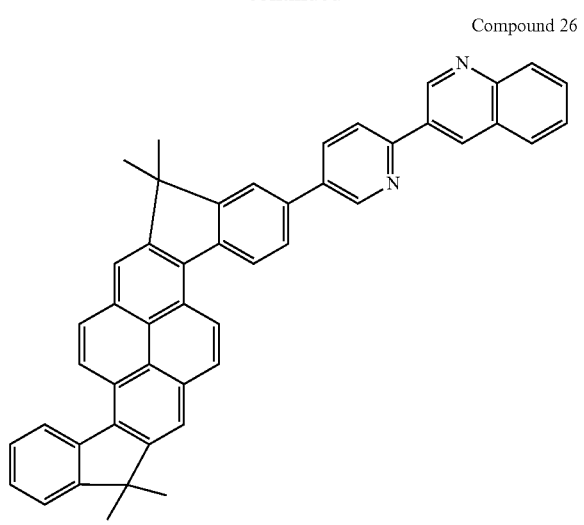
Compound 27
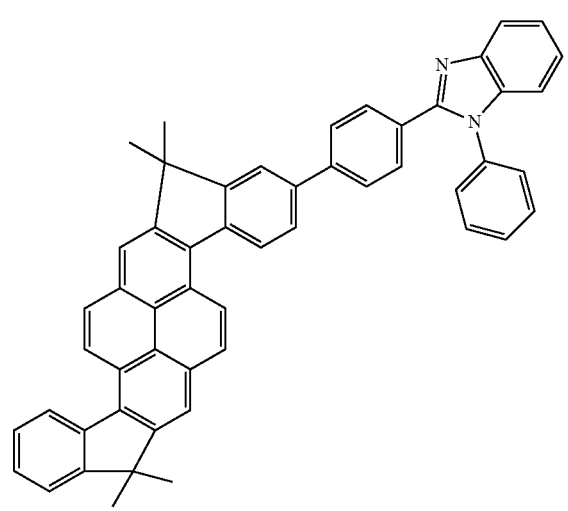
Compound 28
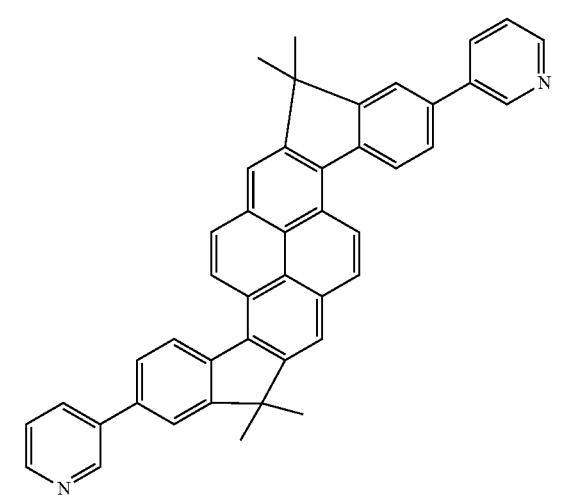
Compound 29
Compound 30
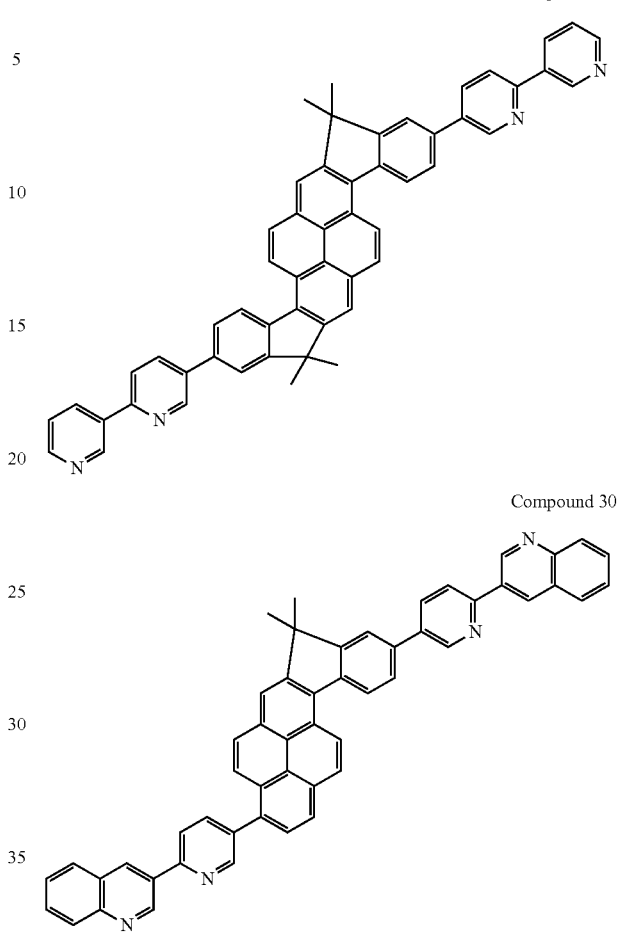
Compound 31
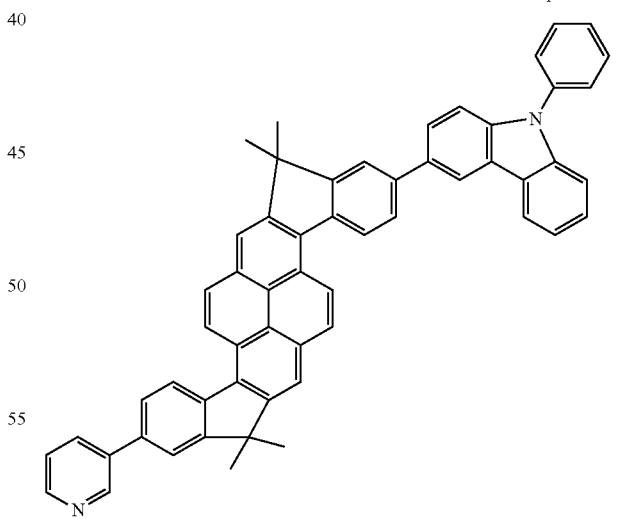

Compound 32
Compound 33
Compound 34
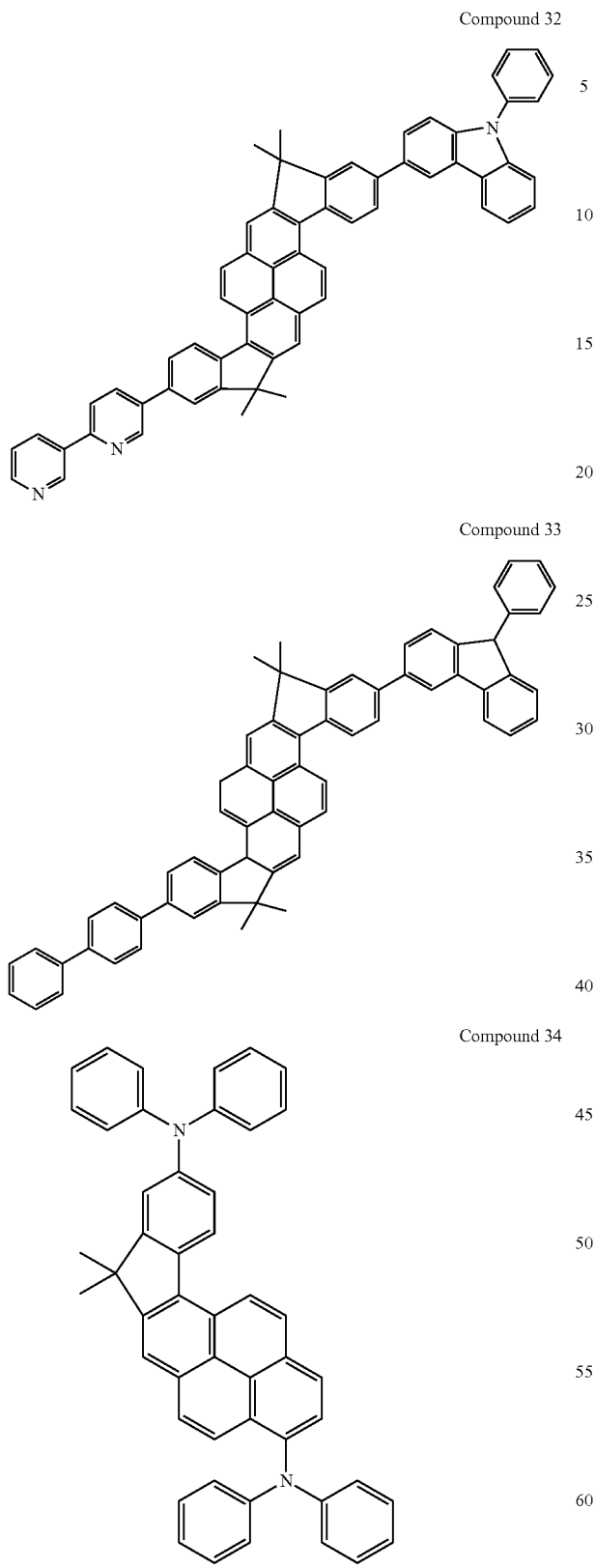
Compound 35
Compound 36
Compound 37
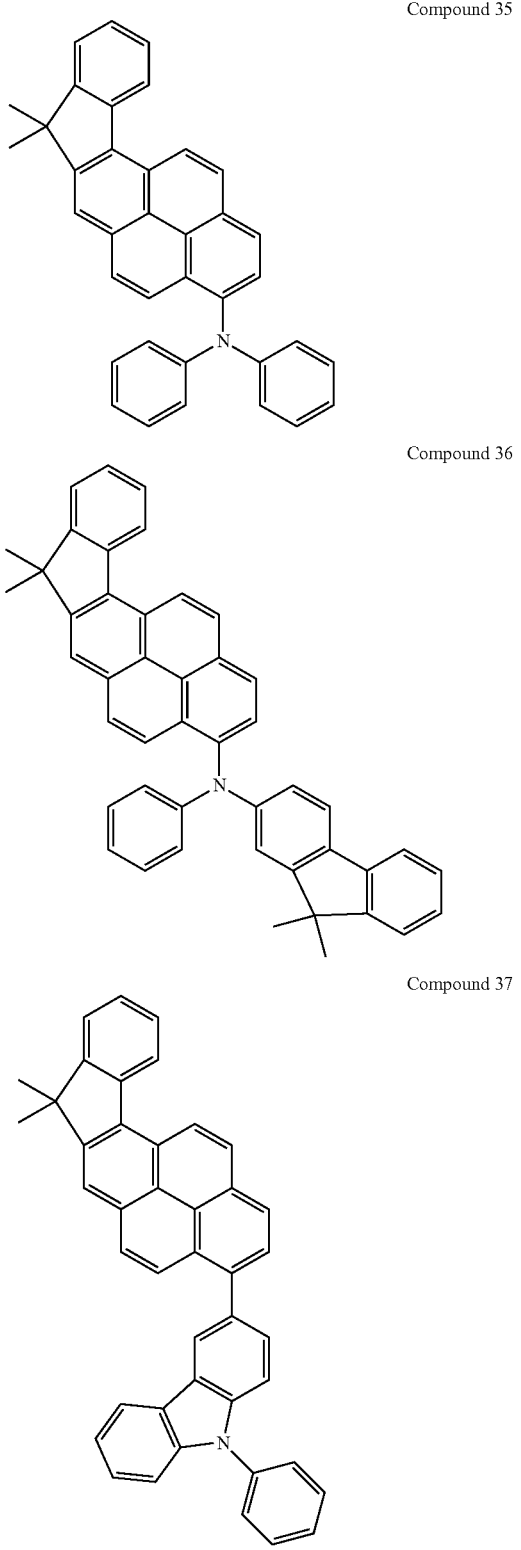

Compound 38
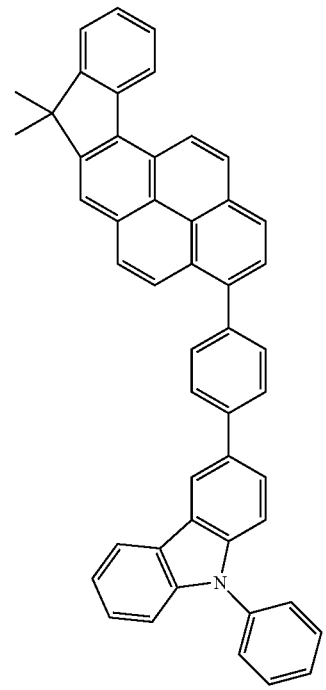
Compound 39
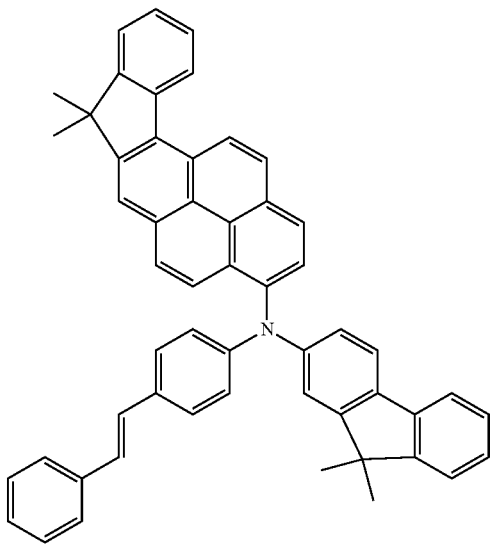
Compound 40
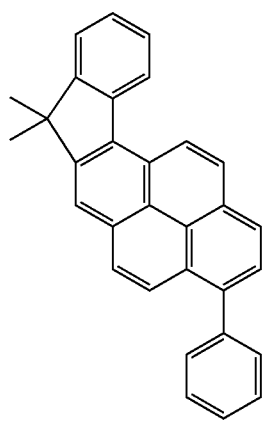
Compound 41
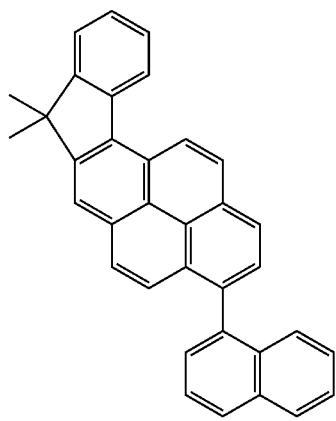
Compound 42
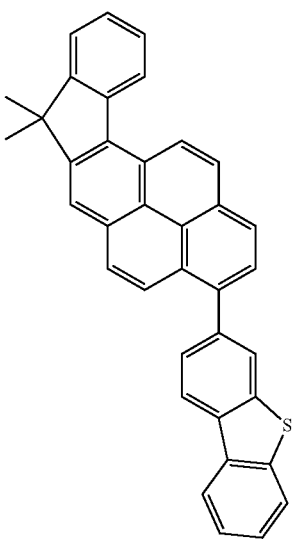

Compound 43

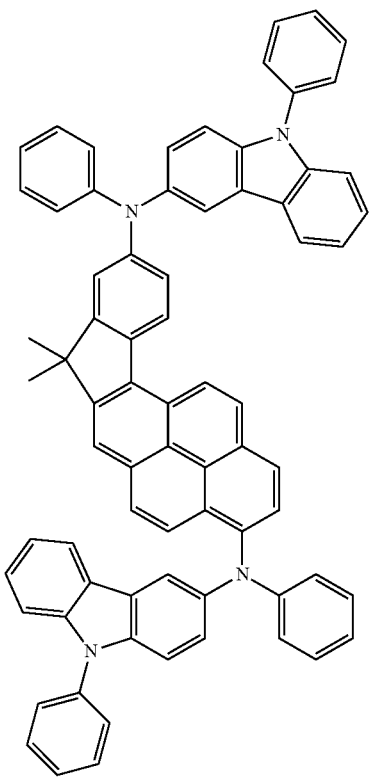

18. An organic light emitting diode comprising:

a first electrode;

a second electrode facing the first electrode; and an organic layer disposed between the first electrode and the second electrode;

wherein the organic layer comprises the condensed-cyclic compound of claim 1.

19. The organic light emitting diode of claim 18, wherein the organic layer is a hole transport layer, an emissive layer, or an electron transport layer.

20. The organic light emitting diode of claim 18, further comprising, between the first electrode and the second electrode, at least one layer selected from the group consisting of a hole injection layer, a hole transport layer, an emissive layer, a hole blocking layer, an electron transport layer, and an electron injection layer.

21. A condensed-cyclic compound represented by Formula 1 below:

Formula 1

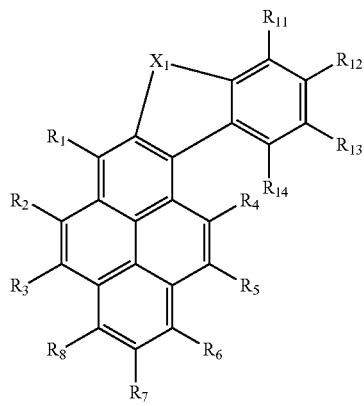

wherein $R_7$ is selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted C1-C30 alkoxy group, a group represented by —$(Ar_1)_a$—$Ar_{11}$, and a group represented by —N[—$(Ar_2)_b$—$Ar_{12}$][—$(Ar_3)_c$—$Ar_{13}$] and $R_8$ is selected from the group consisting of a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_1)_a$—$Ar_{11}$, and a group represented by —N[—$(Ar_2)_b$—$Ar_{12}$][—$(Ar_3)_c$—$Ar_{13}$]; or $R_8$ is connected to * of Formula 2 and $R_7$ is connected to *' of Formula 2 represented by:

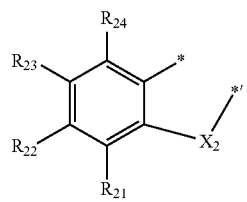

wherein $R_1$ through $R_6$, $R_{11}$ through $R_{14}$, and $R_{21}$ through $R_{24}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a group represented by —$(Ar_4)_d$—$Ar_{14}$, and a group represented by —N[—$(Ar_5)_e$—$Ar_{15}$][—$(Ar_6)_f$—$Ar_{16}$];

wherein $Ar_1$ through $Ar_6$ are each independently selected from the group consisting of a substituted or unsubstituted $C_1$-$C_{30}$ alkylene group, a substituted or unsubstituted $C_2$-$C_{30}$ alkenylene group, a substituted or unsubstituted $C_5$-$C_{30}$ arylene group, and a substituted or unsubstituted $C_4$-$C_{30}$ heteroarylene group;

wherein $Ar_{11}$ is selected from the group consisting of a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group;

wherein $Ar_{12}$ through $Ar_{16}$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted $C_4$-$C_{30}$ heteroaryl group;

wherein a through f are each independently an integer from 0 to 10;

wherein the moieties represented by $Ar_1$ in the group represented by —$(Ar_1)_a$—$Ar_{11}$ are identical to or different from each other, the moieties represented by $Ar_2$ in the group represented by —$(Ar_2)_b$—$Ar_{12}$ are identical to or different from each other, the moieties represented by $Ar_3$ in the group represented by —$(Ar_3)_c$—$Ar_{13}$ are identical to or different from each other, the moieties represented by $Ar_4$ in the group represented by —$(Ar_4)_d$—$Ar_{14}$ are identical to or different from each other, the moieties represented by $Ar_5$ in the group represented by —$(Ar_5)_e$—$Ar_{15}$ are identical to or different from each other, and the moieties represented by $Ar_6$ in the group represented by [—$(Ar_6)_f$—$Ar_{16}$] are identical to or different from each other;

wherein $X_1$ and $X_2$ are each independently a divalent linking group selected from the group consisting of —C($Q_1$)($Q_2$)- and —N($Q_3$)-; and wherein $Q_1$ through $Q_3$ are each independently selected from the group consisting of a hydrogen atom, a halogen atom, a hydroxyl group, a cyano group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryl group, and a substituted or unsubstituted heteroaryl group.

\* \* \* \* \*